(12) United States Patent
Nesvadba et al.

(10) Patent No.: US 8,669,398 B2  
(45) Date of Patent: Mar. 11, 2014

(54) POLYMERISATION INITIATOR

(75) Inventors: Peter Nesvadba, Marly (CH); Lucienne Bugnon Folger, Pfeffingen (CH); Antoine Carroy, Limburgerhof (DE); Marc Faller, Hegenheim (FR)

(73) Assignee: BASF SE, Ludwigshafen (DE)

( * ) Notice: Subject to any disclaimer, the term of this patent is extended or adjusted under 35 U.S.C. 154(b) by 333 days.

(21) Appl. No.: 13/143,355

(22) PCT Filed: Dec. 28, 2009

(86) PCT No.: PCT/EP2009/067947  
§ 371 (c)(1),  
(2), (4) Date: Aug. 11, 2011

(87) PCT Pub. No.: WO2010/079102  
PCT Pub. Date: Jul. 15, 2010

(65) Prior Publication Data  
US 2011/0288251 A1    Nov. 24, 2011

(30) Foreign Application Priority Data  
Jan. 8, 2009 (EP) .................................... 09150183

(51) Int. Cl.  
*C07C 275/70* (2006.01)

(52) U.S. Cl.  
USPC ........ 564/225; 525/333.7; 525/374; 525/375; 525/377; 525/220; 546/184; 558/302; 564/297; 564/301

(58) Field of Classification Search  
USPC ............... 525/333.7, 374, 375, 377; 526/220; 546/184; 558/302; 564/225, 297, 301  
See application file for complete search history.

(56) References Cited

U.S. PATENT DOCUMENTS 6,133,414 A    10/2000    Pfaendner

FOREIGN PATENT DOCUMENTS

| GB | 2 342 649 A | 4/2000 |
|----|-------------|--------|
| WO | 97/49737 A | 12/1997 |
| WO | 00/07981 A | 2/2000 |
| WO | 01/90113 A | 11/2001 |
| WO | 03/004471 A | 1/2003 |
| WO | 2004/081100 A | 9/2004 |
| WO | 2006/051047 A | 5/2006 |

OTHER PUBLICATIONS

CAPlus abstract of Erich Schmidt and Wolfgang Carl, "Aliphatic carbodiimides. XII". Justus Liebigs Annalen der Chemie 1961, 639, 24-31.*

* cited by examiner

*Primary Examiner* — Richard A Huhn  
(74) *Attorney, Agent, or Firm* — Shruti Costales

(57) ABSTRACT

The invention relates to novel O-dialkylamino-isoureas and polymerizable compositions comprising these O-dialkylamino-isoureas of compounds of the general formula (I). The invention further relates to the use of O-dialkylamino-isoureas as polymerization initiators, especially to prepare coatings or for controlled degradation of polyolefins.

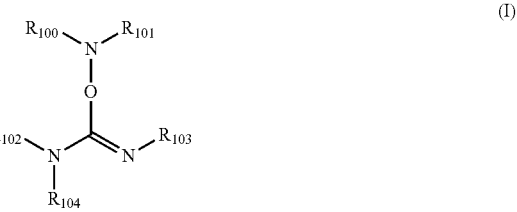

(I)

7 Claims, No Drawings

POLYMERISATION INITIATOR

The invention relates to novel compounds obtained by reacting hydroxylamines with carbodiimides and polymerizable compositions comprising these compounds. The invention further relates to the use of these compounds as polymerization initiators or for controlled degradation of polyolefins.

Free-radical polymerization belongs to the most important polymerization methods. It is used for preparing many commercially important polymers such as polystyrene, PVC, polyacrylates, polymethacrylates, PAN and other polymers. For technical details, reference may be made to the still relevant standard work G. Odian, *Principles of Polymerization*, McGraw-Hill New York 1991.

Free-radical polymerizations are started using initiators. Examples of initiators which have become established in polymer technology are azo compounds, dialkyl peroxides, diacyl peroxides, hydroperoxides, thermolabile C—C-dimers, redox systems and photoinitiators. Reference is made to the "Handbook of Free Radical Initiators", (E. T. Denisov, T. G. Denisova, T. S. Pokidova, J. Wiley & Sons, Inc. Hoboken, N.J., 2003).

Despite their widespread use, these initiators have various disadvantages. Thus, for example, peroxides are extremely readily ignitable and sustain fire and present thus potential explosion hazards, so that their use, storage and transport has to involve costly safety precautions. Some initiators generate toxic products, as e.g. AIBN.

There is therefore a general need for new initiators for free-radical polymerization processes which have a satisfactory safety profile.

The international Publication WO 2001/90113 and WO 2004/081100/A1 describe sterically hindered N-acyloxyamines as a new class of polymerization initiators. Similar to these developments are new N-substituted imides as new polymerization initiators described in WO 2006/051047/A1

We have now discovered that carbodiimides react with sterically hindered N-hydroxyamines to afford the hitherto unknown reaction products which can be most probably characterized to have an O-dialkylamino-isourea structure. Furthermore, these new compounds were found to be very efficient initiators of free radical polymerization or of other processes which are triggered off by free radicals, for example controlled degradation of polyolefines.

The object of the invention are new O-dialkylamino-isoureas compounds of the general formula I

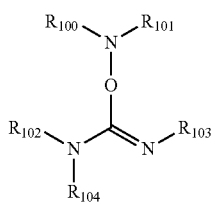

(I)

wherein
$R_{100}$ and $R_{101}$ are each independently of one another $C_1$-$C_{20}$ alkyl or $C_6$-$C_{10}$aryl; or $R_{100}$ and $R_{101}$ form together a mono or polycyclic heterocyclic ring, said heterocyclic ring optionally contains further heteroatoms O, S, N and P;
$R_{102}$ and $R_{103}$ are independently $C_1$-$C_{19}$alkyl, $C_5$-$C_{12}$cycloalkyl, $C_6$-$C_{10}$aryl, $C_7$-$C_{10}$aralkyl, $(CH_3)_3Si$—, said $C_1$-$C_{19}$alkyl, $C_5$-$C_{12}$cycloalkyl, $C_6$-$C_{10}$aryl, $C_7$-$C_{10}$aralkyl group is optionally interrupted by O or N atoms or substituted by $C_1$-$C_{19}$ alkyl groups or substituted by N containing groups selected from $C_1$-$C_{19}$alkylamino, bis($C_1$-$C_{19}$alkyl)amino or tris($C_1$-$C_{19}$alkyl)ammonium;
$R_{104}$ is H, $C_1$-$C_{19}$alkyl, $C_5$-$C_{12}$cycloalkyl, $C_7$-$C_{10}$aralkyl or acyl selected from the group consisting of the following acyls
—C(=O)—H, —C(=O)—$C_1$-$C_{19}$alkyl, —C(=O)—$C_2$-$C_{19}$alkenyl, —C(=O)—$C_6$-$C_{10}$aryl, —C(=O)—$C_2$-$C_{19}$alkenyl-$C_6$-$C_{10}$aryl, —C(=O)—O—$C_1$-$C_{19}$alkyl, —C(=O)—O—$C_6$-$C_{10}$aryl, —C(=O)—NH—$C_1$-$C_{19}$alkyl, —C(=O)—NH—$C_6$-$C_{10}$aryl and —C(=O)—N($C_1$-$C_{19}$alkyl)$_2$.

The structure of (I) can be such (e.g. dimeric, trimeric, oligomeric or polymeric) that the molecule (I) contains the isourea fragment more than once, for example 2 to 10 times.

A preferred embodiment of the invention provides compounds of the formula I wherein
$R_{100}$ and $R_{101}$ are a radical of the formula A

(A)

wherein
$R_1$-$R_4$ are each $C_1$-$C_6$alkyl; or $R_1$ and $R_2$ or/and $R_3$ and $R_4$ can form together with the C-atom to which they are attached a $C_5$-$C_8$ cycloalkyl ring;
$R_5$ and $R_6$ are each, independently of one another, hydrogen, $C_1$-$C_6$alkyl or $C_6$-$C_{10}$aryl; or $R_5$ and $R_6$ are together oxygen;
Q is a direct bond or a bivalent radical —($CR_7R_8$)— or —($CR_7R_8$—$CR_9R_{10}$)—, wherein $R_7$, $R_8$, $R_9$ and $R_{10}$ are each, independently of one another, hydrogen or $C_1$-$C_6$alkyl; and
$Z_1$ is oxygen or a bivalent radical —$NR_{11}$—, wherein $R_{11}$ is hydrogen, $C_1$-$C_6$alkyl, $C_6$-$C_{10}$aryl or an acyl radical selected from the group consisting of —C(=O)—H, —C(=O)—$C_1$-$C_{19}$alkyl, —C(=O)—$C_2$-$C_{19}$alkenyl, —C(=O)—$C_2$-$C_4$alkenyl-$C_6$-$C_{10}$aryl, —C(=O)—$C_6$-$C_{10}$aryl, —C(=O)—O—$C_1$-$C_{19}$alkyl, —C(=O)—O—$C_6$-$C_{10}$aryl, —C(=O)—NH—$C_1$-$C_{19}$alkyl, —C(=O)—NH—$C_6$-$C_{10}$aryl and —C(=O)—N($C_1$-$C_{19}$alkyl)$_2$; or
$Z_1$ is —($CR_{12}R_{13}$)—, where independently of one another one of the radicals $R_{12}$ and $R_{13}$ is hydrogen or $C_1$-$C_6$alkyl and the other is —OH, —$NH_2$, COOH, —CN, $C_1$-$C_6$alkyl, $C_1$-$C_{19}$alkoxy, $C_6$-$C_{10}$aryloxy, or monoacyloxy selected from the group consisting of
—O—C(=O)—H, —O—C(=O)—$C_1$-$C_{19}$alkyl, —O—C(=O)—$C_2$-$C_{19}$alkenyl, —O—C(=O)—$C_6$-$C_{10}$aryl, —O—C(=O)—$C_2$-$C_{19}$alkenyl-$C_6$-$C_{10}$aryl, —O—C(=O)—O—$C_1$-$C_{19}$alkyl, —O—C(=O)—O—$C_6$-$C_{10}$aryl, —O—C(=O)—NH—$C_1$-$C_{19}$alkyl, —O—C(=O)—NH—$C_6$-$C_{10}$aryl and —O—C(=O)—N($C_1$-$C_{19}$alkyl)$_2$, or
diacyloxy selected from —O—C(=O)—$(CH_2)_q$—C(=O)—O— (q=0-12), ortho-, meta-, or para-$C_6H_4$(COO—)$_2$, or
triacyloxy of the formula 1,3,5-$C_6H_3$(COO—)$_3$, or
$C_1$-$C_{19}$alkylamino, di-$C_1$-$C_{19}$alkylamino, $C_6$-$C_{10}$arylamino, acylamino selected from the group consisting of —NH—C(=O)—H, —NH—C(=O)—C$_1$-C$_{19}$alkyl, —NH—C(=O)—C$_2$-C$_{19}$alkenyl, —NH—C(=O)—C$_6$-C$_{10}$aryl, —NH—C(=O)—C$_2$-C$_{19}$alkenyl-C$_6$-C$_{10}$aryl, —NH—C(=O)—O—C$_1$-C$_{19}$alkyl, —NH—C(=O)—O—C$_6$-C$_{10}$aryl, —NH—C(=O)—NH—C$_1$-C$_{19}$alkyl, —NH—C(=O)—NH—C$_6$-C$_{10}$aryl and —NH—C(=O)—N(C$_1$-C$_{19}$alkyl)$_2$, diacylamino selected from the group consisting of —N[—C(=O)—C$_1$-C$_{19}$alkyl]$_2$ and —N[—C(=O)—C$_6$-C$_{10}$aryl]$_2$, or N-acyl-N—C$_1$-C$_{19}$alkylamino, or bis(acylamino) selected from —NH—C(=O)—(CH$_2$)$_q$—C(=O)—NH— (q=0-12), ortho-, meta-, or para-C$_6$H$_4$(CONH—)$_2$, or tris(acylamino) of the formula 1,3,5-C$_6$H$_3$(CONH—)$_3$ or the two radicals R$_{12}$ and R$_{13}$ are together oxo, or the two radicals R$_{12}$ and R$_{13}$ form together with the C atom to which they are bound a 5 or 6 membered ring containing up to two oxygen atoms or one oxygen atom and a group —NR$_{11}$—;

said 5 or 6 membered ring is optionally substituted by one or independently of each other two of the groups consisting of C$_1$-C$_{19}$alkyl, —CH$_2$OH, or —CH$_2$-acyloxy selected from the group consisting of the following acyloxyls —O—C(=O)—H, —O—C(=O)—C$_1$-C$_{19}$alkyl, —O—C(=O)—C$_2$-C$_{19}$alkenyl, —O—C(=O)—C$_6$-C$_{10}$aryl, —O—C(=O)—C$_2$-C$_{19}$alkenyl-C$_6$-C$_{10}$aryl, —O—C(=O)—O—C$_1$-C$_{19}$alkyl, —O—C(=O)—O—C$_6$-C$_{10}$aryl, —O—C(=O)—NH—C$_1$-C$_{19}$alkyl, —O—C(=O)—NH—C$_6$-C$_{10}$aryl and —O—C(=O)—N(C$_1$-C$_{19}$alkyl)$_2$.;

furthermore, this 5 or 6 membered ring may be linked to a second 5-8 membered carbocyclic ring;

R$_{102}$ and R$_{103}$a are independently C$_1$-C$_4$alkyl, C$_5$-C$_6$cycloalkyl, C$_6$-C$_7$aryl, C$_7$-C$_{10}$aralkyl, R$_{104}$ is H, C$_1$-C$_8$alkyl, C$_5$-C$_6$cycloalkyl, C$_7$-aralkyl or acyl selected from the group consisting of the following acyls —C(=O)—C$_1$-C$_{17}$alkyl, —C(=O)—C$_2$-C$_3$alkenyl, —C(=O)—C$_6$-C$_{10}$aryl, —C(=O)—O—C$_1$-C$_8$alkyl, —C(=O)—NH—C$_1$-C$_8$alkyl, —C(=O)—NH—C$_6$-C$_{10}$aryl and —C(=O)—N(C$_1$-C$_8$alkyl)$_2$.

The term in the definition of Z$_1$ in formula Ia "or the two radicals R$_{12}$ and R$_{13}$ form together with the C atom to which they are bound a 5 or 6 membered ring containing up to two oxygen atoms or one oxygen atom and a group —NR$_{11}$—". result in structures like:

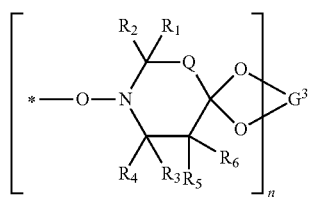

1C wherein n is 1 or 2 and R$_1$-R$_6$ and Q are as defined under formula A

G$^3$ is C$_2$-C$_8$alkylene, C$_2$-C$_8$hydroxyalkylene or C$_4$-C$_{22}$acyloxyalkylene when n=1 or is the group (—CH$_2$)$_2$C(CH$_2$)$_2$ when n=2.

or in a structure like

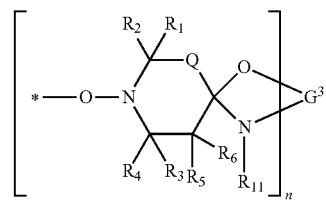

1D wherein n is 1 or 2 and R$_1$-R$_6$ and R$_{11}$ and Q are as defined under formula A G$^3$ is C$_2$-C$_8$alkylene, C$_2$-C$_8$hydroxyalkylene or C$_4$-C$_{22}$acyloxyalkylene or C$_2$-C$_8$-dihydroxyalkylene or C$_4$-C$_{22}$bisacyloxyalkylene;

or in a structure like

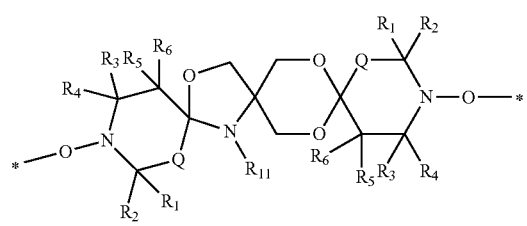

1E wherein R$_1$-R$_6$ and R$_{11}$ and Q are as defined under formula A or in a structure like

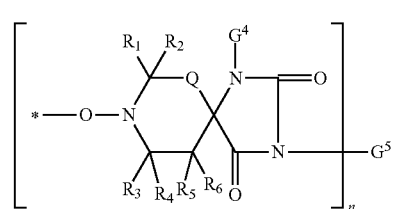

1F wherein R$_1$-R$_6$ and Q are as defined under formula A

G$^4$ is hydrogen, C$_1$-C$_{19}$alkyl, allyl, benzyl, glycidyl or C$_2$-C$_6$alkoxyalkyl; and G$^5$ has the following meanings:

when n=1, hydrogen, C$_1$-C$_{19}$alkyl, C$_3$-C$_5$alkenyl, C$_7$-C$_9$aralkyl, C$_5$-C$_7$cycloalkyl, C$_2$-C$_4$hydroxyalkyl, C$_2$-C$_6$alkoxyalkyl, C$_6$-C$_{10}$aryl, glycidyl or a group: —(CH$_2$)$_p$—COO-Q or —(CH$_2$)$_p$—O—CO-Q, where p is 1 or 2 and Q is C$_1$-C$_{19}$alkyl or phenyl; or when n=2, C$_2$-C$_{12}$alkylene, C$_4$-C$_{12}$alkenylene, C$_6$-C$_{12}$arylene, the group —CH$_2$—CH(OH)—CH$_2$—O-D-O—CH$_2$—CH(OH)—CH$_2$—, where D is C$_2$-C$_{10}$-alkylene, C$_6$-C$_{15}$arylene or C$_6$-C$_{12}$-cycloalkylene, or the group —CH$_2$CH(OZ')CH$_2$—(OCH$_2$—CH(OZ')CH$_2$)$_2$—, where Z' is hydrogen, C$_1$-C$_{18}$alkyl, allyl, benzyl, C$_2$-C$_{12}$-alkanoyl or benzoyl.

or in a structure like

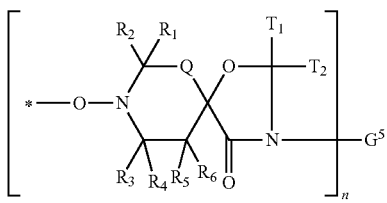

wherein n is 1 or 2 and $R_1$-$R_6$ and Q are as defined under formula A $G^5$ has the following meanings:

when n=1,
hydrogen, $C_1$-$C_{19}$alkyl, $C_3$-$C_5$alkenyl, $C_7$-$C_9$aralkyl, $C_5$-$C_7$cycloalkyl, $C_2$-$C_4$hydroxyalkyl, $C_2$-$C_6$alkoxyalkyl, $C_6$-$C_{10}$aryl, glycidyl or a group: —$(CH_2)_p$—COO-Q or —$(CH_2)_p$—O—CO-Q, where p is 1 or 2 and Q is $C_1$-$C_{19}$alkyl or phenyl; or when n=2,
$C_2$-$C_{12}$alkylene, $C_4$-$C_{12}$alkenylene, $C_6$-$C_{12}$arylene, the group —$CH_2$—CH(OH)—$CH_2$—O-D-O—$CH_2$—CH(OH)—$CH_2$—, where D is $C_2$-$C_{10}$-alkylene, $C_6$-$C_{15}$arylene or $C_6$-$C_{12}$-cycloalkylene, or the group —$CH_2CH(OZ')CH_2$—$(OCH_2$—$CH(OZ')CH_2)_2$—, where Z' is hydrogen, $C_1$-$C_{18}$alkyl, allyl, benzyl, $C_2$-$C_{12}$-alkanoyl or benzoyl;

$T^1$ and $T^2$ are each, independently of one another, hydrogen, $C_1$-$C_{19}$alkyl, $C_6$-$C_{10}$aryl or $C_7$-$C_9$aralkyl, each of which may be substituted by halogen or $C_1$-$C_4$-alkyl, or $T^1$ and $T^2$ together with the carbon atom connecting them form a $C_5$-$C_{14}$cycloalkane ring;

or in a structure like

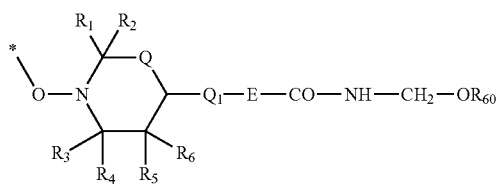

wherein $R_1$-$R_6$ and Q are as defined under formula A $Q_1$ is —NH or —N—$C_1$-$C_{18}$alkyl or —O—;

E is $C_1$-$C_3$, the group —$CH_2CH(R_8)$—O— wherein $R_8$ is hydrogen, methyl or phenyl, the group —$(CH_2)_3$—NH—; or E is a direct bond;

$R_{60}$ is $C_1$-$C_{18}$alkyl, $C_5$-$C_7$-cycloalkyl, $C_7$-$C_{12}$aralkyl, cyanoethyl, $C_6$-$C_{10}$-aryl, the group —$CH_2CH(R_8)$—OH; wherein $R_8$ is hydrogen, methyl or phenyl, the group —$(CH_2)_3$—NH—; or $R_{60}$ is a group of the formula

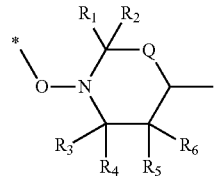

wherein $R_1$-$R_6$ and Q are as defined under formula Ia; or $R_{60}$ is a group of the formula

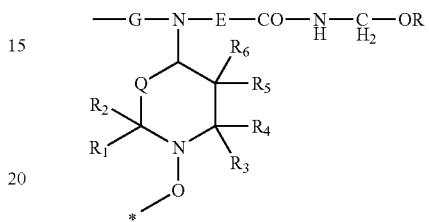

wherein $R_1$-$R_6$ and Q are as defined under formula A

E is $C_1$-$C_3$, the group —$CH_2CH(R_8)$—O— wherein $R_8$ is hydrogen, methyl or phenyl, the group —$(CH_2)_3$—NH—; or E is a direct bond;

G is $C_2$-$C_6$ or $C_6$-$C_{12}$arylene and R is hydrogen, $C_1$-$C_{18}$alkyl which is uninterrupted or $C_2$-$C_{18}$alkyl which is interrupted by one or more oxygen atoms, cyanoethyl, benzoyl, glycidyl, a monovalent radical of an aliphatic carboxylic acid having 2 to 18 carbon atoms, of a cycloaliphatic carboxylic acid having 7 to 15 carbon atoms, of an αβ-unsaturated carboxylic acid having 3 to 5 carbon atoms or of an aromatic carboxylic acid having 7 to 15 carbon atoms, where each carboxylic acid can be substituted in the aliphatic, cycloaliphatic or aromatic moiety by 1 to 3-$COOZ_{12}$ groups, in which $Z_{12}$ is H, $C_1$-$C_{20}$-alkyl, $C_3$-$C_{12}$alkenyl, $C_5$-$C_7$cycloalkyl, phenyl or benzyl; or R is a monovalent radical of a carbamic acid or phosphorus-containing acid or a monovalent silyl radical;

or $R_{60}$ is a group -E-CO—NH—$CH_2$—Oh or group -E-CO—NH—$CH_2$—O—$C_1$-$C_{18}$alkyl; wherein E is —$CH_2CH(R_8)$—O— wherein $R_8$ is hydrogen, methyl or phenyl, the group —$(CH_2)_3$—NH—; or E is a direct bond;

or in a structure like

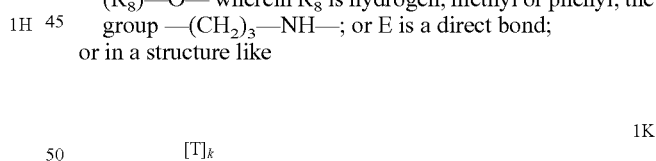

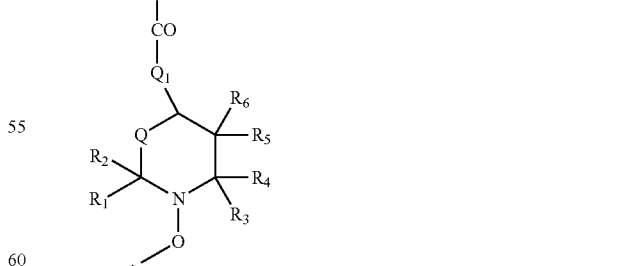

wherein $R_1$-$R_6$ and Q are as defined under formula A k is 2 to 100;

T is ethylene or 1,2-propylene, or is a repeating structural unit derived from an α-olefin copolymer with an alkyl acrylate or methacrylate; and $Q_1$ is —NH or —N—$C_1$-$C_{18}$alkyl or —O—;
or in a structure like

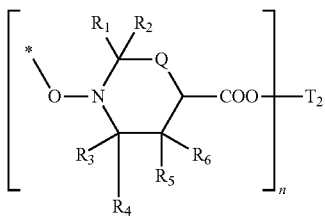

1L wherein $R_1$-$R_6$ and Q are as defined under formula A $T_2$ if n is 1, is hydrogen, $C_1$-$C_{12}$alkyl, $C_3$-$C_5$alkenyl, $C_7$-$C_9$aralkyl, $C_5$-$C_7$cycloalkyl, $C_2$-$C_4$hydroxyalkyl, $C_2$-$C_6$alkoxyalkyl, $C_6$-$C_{10}$aryl, glycidyl, a group of formula —$(CH_2)_m$—COO-Q or of the formula —$(CH_2)_m$, —O—CO-Q wherein m is 1 or 2 and Q is $C_1$-$C_4$alkyl or phenyl; or;

$T_2$ if n is 2, is $C_2$-$C_{12}$, $C_6$-$C_{12}$arylene, a group —$CH_2CH(OH)CH_2$—O-D-O—$CH_2CH(OH)CH_2$— wherein D is $C_2$-$C_{10}$, $C_6$-$C_{15}$arylene or $C_6$-$C_{12}$cyclo, or a group —$CH_2CH(OZ_1)CH_2$—$(OCH_2CH(OZ_1)CH_2)_2$— wherein $Z_1$ is hydrogen, $C_1$-$C_{18}$alkyl, allyl, benzyl, $C_2$-$C_{12}$alkanoyl or benzoyl;

or in a structure like

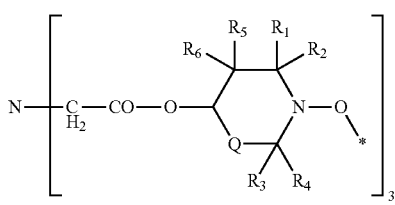

1M wherein $R_1$-$R_6$ and Q are as defined under formula A;
or in a structure like

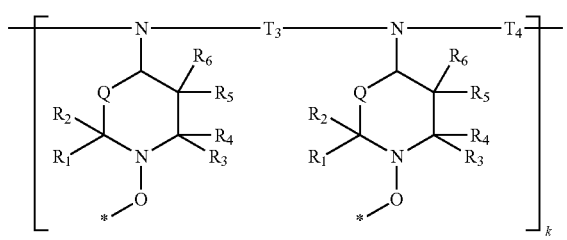

1N wherein $R_1$-$R_6$ and Q are as defined under formula A
k is 2 to 100;

$T_3$ and $T_4$ are independently of one another $C_2$-$C_{12}$alkylene, or $T_4$ is a group

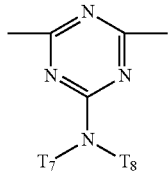

$T_7$ and $T_8$ are independently of one another hydrogen $C_1$-$C_{18}$alkyl, or $T_7$ and $T_8$ together are $C_4$-$C_6$ or 3-oxapenthamethylene;

or in a structure like

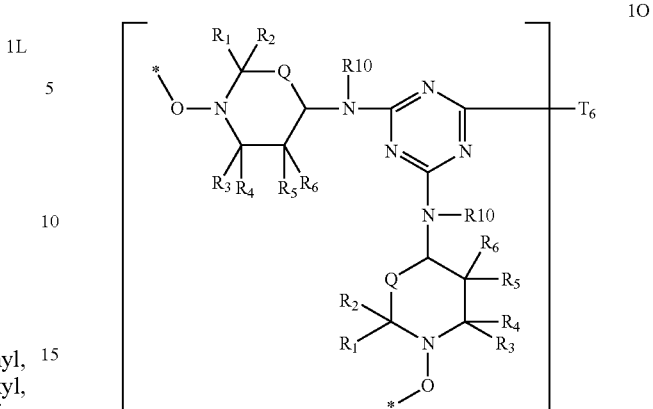

1O wherein $R_1$-$R_6$ and Q are as defined under formula A
e is 3 or 4;
$T_6$ is

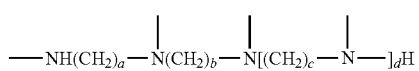

wherein a, b and c are independently 2 or 3, and d is 0 or 1;
$R_{10}$ is hydrogen $C_1$-$C_{12}$alkyl, $C_5$-$C_7$cycloalkyl, $C_7$-$C_8$aralkyl, $C_2$-$C_{18}$alkanoyl, $C_3$-$C_5$alkenoyl or benzoyl; preferably hydrogen or $C_1$-$C_{12}$alkyl;
or in a structure like

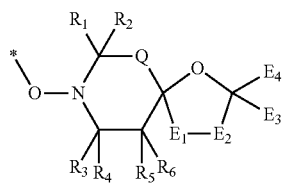

1P wherein $R_1$-$R_6$ and Q are as defined under formula A $E_1$ and $E_2$, being different, each are —CO— or —N($E_5$)-, wherein $E_5$ is hydrogen, $C_1$-$C_{12}$alkyl or $C_4$-$C_{22}$alkoxycarbonylalkyl;

$E_3$ and $E_4$ independently of one another are hydrogen, $C_1$-$C_{30}$alkyl, unsubstituted phenyl or naphthyl; or phenyl or naphthyl substituted by chlorine or by $C_1$-$C_4$alkyl;

$E_3$ and $E_4$ together are polymethylene of 4 to 17 carbon atoms, optionally substituted by up to four $C_1$-$C_4$alkyl groups;
or in a structure like

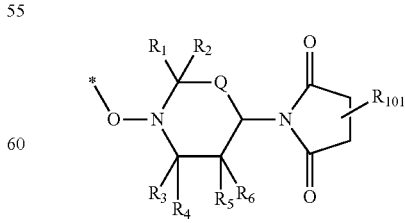

1Q wherein $R_1$-$R_6$ and Q are as defined under formula A
$R_{101}$ is $C_1$-$C_{12}$alkyl, $C_5$-$C_7$cycloalkyl, $C_7$-$C_8$aralkyl, $C_2$-$C_{18}$alkanoyl, $C_3$-$C_5$alkenoyl or benzoyl;

or in a structure like

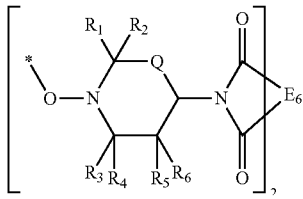

wherein $R_1$-$R_6$ and Q are as defined under formula A $E_6$ is an aliphatic or aromatic tetravalent radical;

A tetravalent radical is, for example, the tetravalent radical of butane-1,2,3,4-tetracarboxylic acid or of pyromellitic acid;

or in a structure like

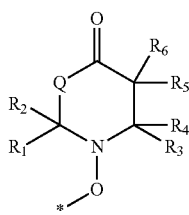

wherein $R_1$-$R_6$ and Q are as defined under formula A;

or in a structure like

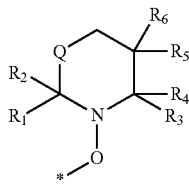

wherein $R_1$-$R_6$ and Q are as defined under formula A;

or in a structure like

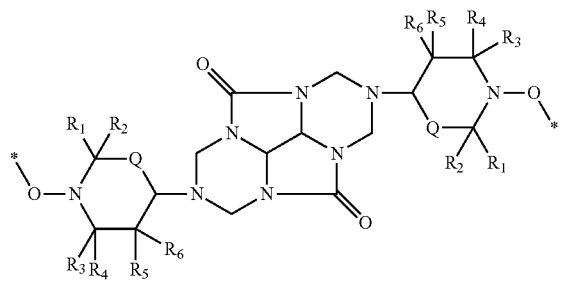

wherein $R_1$-$R_6$ and Q are as defined under formula A;

or in a structure like

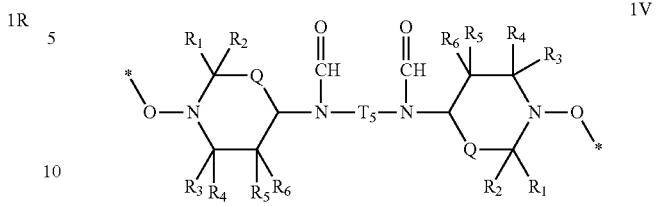

wherein $R_1$-$R_6$ and Q are as defined under formula A $T_5$ is $C_2$-$C_{22}$, $C_5$-$C_7$cyclo, $C_1$-$C_4$di($C_5$-$C_7$cyclo), phenylene or phenylenedi($C_1$-$C_4$);

or in a structure like

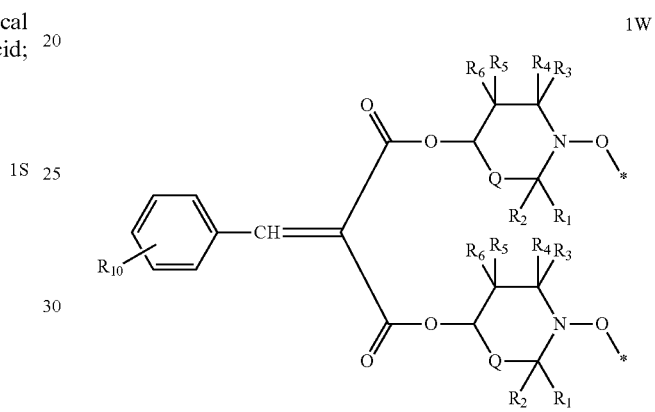

wherein $R_1$-$R_6$ and Q are as defined under formula A $R_{10}$ is hydrogen, $C_1$-$C_{12}$alkyl or $C_1$-$C_{12}$alkoxy.

A particularly preferred embodiment of the invention provides compounds of the formula I wherein $R_{100}$ and $R_{101}$ are each independently of one another $C_1$-$C_4$alkyl or form together a radical of the formula A

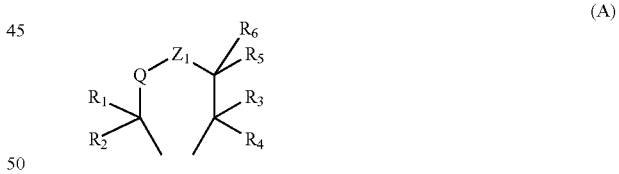

wherein $R_1$-$R_4$ are each $C_1$-$C_6$alkyl; or $R_1$ and $R_2$ or/and $R_3$ and $R_4$ can form together with the C-atom to which they are attached a $C_5$-$C_8$ cycloalkyl ring;

$R_5$ and $R_6$ are each, independently of one another, hydrogen, $C_1$-$C_6$alkyl or $C_6$-$C_{10}$aryl; or $R_5$ and $R_6$ are together oxygen;

Q is a direct bond or a bivalent radical —($CR_7R_8$)— or —($CR_7R_8$—$CR_9R_{10}$)—, wherein $R_7$, $R_8$, $R_9$ and $R_{10}$ are each, independently of one another, hydrogen or $C_1$-$C_6$alkyl; and $Z_1$ is oxygen or a bivalent radical —$NR_{11}$—, wherein $R_{11}$ is hydrogen, $C_1$-$C_6$alkyl, $C_6$-$C_{10}$aryl or an acyl radical selected from the group consisting of —C(=O)—H, —C(=O)—$C_1$-$C_{19}$alkyl, —C(=O)—$C_2$-$C_{19}$alkenyl, —C(=O)—$C_2$-$C_4$alkenyl-$C_6$-$C_{10}$aryl, —C(=O)—$C_6$-

$C_{10}$aryl, —C(=O)—O—$C_1$-$C_{19}$alkyl, —C(=O)—O—$C_6$-$C_{10}$aryl, —C(=O)—NH—$C_1$-$C_{19}$alkyl, —C(=O)—NH—$C_6$-$C_{10}$aryl and —C(=O)—N($C_1$-$C_{19}$alkyl)$_2$; or $Z_1$ is —(CR$_{12}$R$_{13}$)—, where independently of one another one of the radicals $R_{12}$ and $R_{13}$ is hydrogen or $C_1$-$C_6$alkyl and the other is —OH, —NH$_2$, COOH, —CN, $C_1$-$C_6$alkyl, $C_1$-$C_{19}$alkoxy, $C_6$-$C_{10}$aryloxy, or monoacyloxy selected from the group consisting of —O—C(=O)—H, —O—C(=O)—$C_1$-$C_{19}$alkyl, —O—C(=O)—$C_2$-$C_{19}$alkenyl, —O—C(=O)—$C_6$-$C_{10}$aryl, —O—C(=O)—$C_2$-$C_{19}$alkenyl-$C_6$-$C_{10}$aryl, —O—C(=O)—O—$C_1$-$C_{19}$alkyl, —O—C(=O)—O—$C_6$-$C_{10}$aryl, —O—C(=O)—NH—$C_1$-$C_{19}$alkyl, —O—C(=O)—NH—$C_6$-$C_{10}$aryl and —O—C(=O)—N($C_1$-$C_{19}$alkyl)$_2$, or diacyloxy selected from —O—C(=O)—(CH$_2$)$_q$—C(=O)—O— (q=0-12), ortho-, meta-, or para-$C_6H_4$(COO—)$_2$, or triacyloxy of the formula 1,3,5-$C_6H_3$(COO—)$_3$, or $C_1$-$C_{19}$alkylamino, di-$C_1$-$C_{19}$alkylamino, $C_6$-$C_{10}$arylamino, acylamino selected from the group consisting of —NH—C(=O)—H, —NH—C(=O)—$C_1$-$C_{19}$alkyl, —NH—C(=O)—$C_2$-$C_{19}$alkenyl, —NH—C(=O)—$C_6$-$C_{10}$aryl, —NH—C(=O)—$C_2$-$C_{19}$alkenyl-$C_6$-$C_{10}$aryl, —NH—C(=O)—O—$C_1$-$C_{19}$alkyl, —NH—C(=O)—O—$C_6$-$C_{10}$aryl, —NH—C(=O)—NH—$C_1$-$C_{19}$alkyl, —NH—C(=O)—NH—$C_6$-$C_{10}$aryl and —NH—C(=O)—N($C_1$-$C_{19}$alkyl)$_2$, diacylamino selected from the group consisting of —N[—C(=O)—$C_1$-$C_{19}$alkyl]$_2$ and —N[—C(=O)—$C_6$-$C_{10}$aryl]$_2$, or N-acyl-N—$C_1$-$C_{19}$alkylamino, or bis(acylamino) selected from —NH—C(=O)—(CH$_2$)$_q$—C(=O)—NH— (q=0-12), ortho-, meta-, or para-$C_6H_4$(CONH—)$_2$, or tris(acylamino) of the formula 1,3,5-$C_6H_3$(CONH—)$_3$ or the two radicals $R_{12}$ and $R_{13}$ are together oxo, or the two radicals $R_{12}$ and $R_{13}$ form together with the C atom to which they are bound a 5 or 6 membered ring containing up to two oxygen atoms or one oxygen atom and a group —NR$_{11}$—.;

said 5 or 6 membered ring is optionally substituted by one or independently of each other two of the groups consisting of $C_1$-$C_{19}$alkyl, —CH$_2$OH, or —CH$_2$-acyloxy selected from the group consisting of the following acyloxyls —O—C(=O)—H, —O—C(=O)—$C_1$-$C_{19}$alkyl, —O—C(=O)—$C_2$-$C_{19}$alkenyl, —O—C(=O)—$C_6$-$C_{10}$aryl, —O—C(=O)—$C_2$-$C_{19}$alkenyl-$C_6$-$C_{10}$aryl, —O—C(=O)—O—$C_1$-$C_{19}$alkyl, —O—C(=O)—O—$C_6$-$C_{10}$aryl, —O—C(=O)—NH—$C_1$-$C_{19}$alkyl, —O—C(=O)—NH—$C_6$-$C_{10}$aryl and —O—C(=O)—N($C_1$-$C_{19}$alkyl)$_2$.;

furthermore, this 5 or 6 membered ring may be linked to a second 5-8 membered carbocyclic ring;

$R_{102}$ and $R_{103}$a are independently $C_1$-$C_4$alkyl, $C_5$-$C_6$cycloalkyl, $C_6$-$C_7$aryl, $C_7$-$C_{10}$aralkyl, $R_{104}$ is H, $C_1$-$C_8$alkyl, $C_5$-$C_6$cycloalkyl, $C_7$-aralkyl or acyl selected from the group consisting of the following acyls —C(=O)—$C_1$-$C_{17}$alkyl, —C(=O)—$C_2$-$C_3$alkenyl, —C(=O)—$C_6$-$C_{10}$aryl, —C(=O)—O—$C_1$-$C_8$alkyl, —C(=O)—NH—$C_1$-$C_8$alkyl, —C(=O)—NH—$C_6$-$C_{10}$aryl and —C(=O)—N($C_1$-$C_8$alkyl)$_2$.

Of interest are also compounds of the formula I wherein $R_{100}$ and $R_{101}$ are each independently of one another $C_1$-$C_4$alkyl or form together a radical of the formula A

wherein $R_1$-$R_4$ are each $C_1$-$C_2$alkyl;

$R_5$ and $R_6$ are each, independently of one another, hydrogen or methyl;

Q is a bivalent radical —(CH$_2$)—; and $Z_1$ is a bivalent radical —(CR$_{12}$R$_{13}$)—, where one of the radicals $R_{12}$ and $R_{13}$ is hydrogen and the other is H, OH, NH$_2$, acyloxy selected from the group consisting of —O—C(=O)—$C_1$-$C_{17}$alkyl, —O—C(=O)—N($C_1$-$C_6$alkyl)$_2$; benzoyl, or $C_1$-$C_6$alkylamino, di-$C_1$-$C_6$alkylamino, $C_6$-$C_{10}$arylamino, acylamino selected from the group consisting —NH—C(=O)—$C_1$-$C_{17}$alkyl, —NH—C(=O)-phenyl, —NH—C(=O)—N($C_1$-$C_6$alkyl)$_2$, $R_{102}$ and $R_{103}$ are independently $C_1$-$C_3$alkyl, cyclohexyl, phenyl, p-tolyl, 2,6-diisopropylphenyl;

$R_{104}$ is H, $C_1$-$C_4$alkyl, $C_5$-$C_6$cycloalkyl, benzyl or acyl selected from the group consisting of the following acyls —C(=O)—$C_1$-$C_{17}$alkyl and —C(=O)-phenyl.

Of special interest are compounds of the formula I wherein $R_{102}$ and $R_{103}$ are independently $C_1$-$C_3$alkyl, cyclohexyl, phenyl, p-tolyl, 2,6-diisopropylphenyl.

Of particular interest are compounds of the formula I wherein $R_{104}$ is H, $C_1$-$C_4$alkyl, $C_5$-$C_6$cycloalkyl, benzyl or acyl selected from the group consisting of the following acyls —C(=O)—$C_1$-$C_{17}$alkyl and —C(=O)-phenyl.

Of very special interest are compounds of the formula I wherein $R_{100}$ and $R_{101}$ are each independently of one another $C_1$-$C_4$alkyl or form together a radical of the formula A

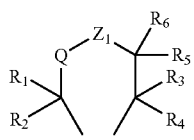

wherein $R_1$-$R_4$ are each, independently of one another, $C_1$-$C_4$alkyl, $R_5$ and $R_6$ are each, independently of one another, hydrogen or $C_1$-$C_4$alkyl;

Q is a bivalent radical —(CR$_7$R$_8$)—, wherein $R_7$ and $R_8$ are each, independently of one another, hydrogen or $C_1$-$C_4$alkyl;

$Z_1$ is —(CR$_{12}$R$_{13}$)—, where independently of one another one of the radicals $R_{12}$ and $R_{13}$ is hydrogen or $C_1$-$C_4$alkyl and the other is —OH, $C_1$-$C_6$alkyl or monoacyloxy selected from the group consisting of —O—C(=O)—H, —O—C(=O)—$C_1$-$C_4$alkyl and —O—C(=O)—$C_6$-$C_{10}$aryl; or diacyloxy selected from —O—C(=O)—(CH$_2$)$_q$—C(=O)—O— (q=0-12) and ortho-, meta- or para-$C_6H_4$(COO—)$_2$;

$R_{102}$ and $R_{103}$ are each, independently of one another, $C_1$-$C_4$alkyl, cyclohexyl, unsubstituted or with $C_1$-$C_4$alkyl substituted phenyl; and $R_{104}$ is hydrogen, —C(=O)—$C_1$-$C_{17}$alkyl or —C(=O)—$C_6$-$C_{10}$aryl.

These compounds are suitable as polymerization initiators, particularly for use in polymerization processes to prepare coatings. The term polymer encompasses oligomers, cooligomers, polymers and copolymers, for example random block, multiblock, star or gradient copolymers.

The compounds can also be used for controlled degradation of polyolefins.

Definition of the Radicals $C_1$-$C_{20}$alkyl in the compound of formula I is, for example, $C_1$-$C_6$alkyl, e.g. methyl, ethyl, n-propyl or isopropyl or n-, sec- or tert-butyl or straight-chain or branched pentyl or hexyl, or $C_7$-$C_{19}$alkyl, e.g. straight-chain or branched heptyl, octyl, isooctyl, nonyl, tert-nonyl, decyl or undecyl, n-tridecyl, n-tetradecyl, n-hexadecyl or n-octadecyl.

$C_6$-$C_{10}$aryl is, for example, carbocyclic monoaryl or diaryl, preferably monoaryl, e.g. phenyl, which may be monosubstituted or disubstituted by suitable substituents, e.g. $C_1$-$C_4$alkyl, e.g. methyl, ethyl or tert-butyl, $C_1$-$C_4$alkoxy, e.g. methoxy or ethoxy, or halogen, e.g. chlorine. In the case of disubstitution, the 2- and 6-positions are preferred.

$C_2$-$C_{19}$alkenyl is for example ethenyl, propenyl, butenyl, pentenyl, hexenyl, heptenyl, octenyl, dodecenyl and the like including their isomers.

$C_7$-$C_{10}$aralkyl is for example benzyl, phenylpropyl, α,α-dimethylbenzyl or α-methylbenzyl.

$C_2$-$C_{12}$alkyl interrupted by at least one O atom is for example —$CH_2$—$CH_2$—O—$CH_2$—$CH_3$, —$CH_2$—$CH_2$—O—$CH_3$ or —$CH_2$—$CH_2$—O—$CH_2$—$CH_2$—$CH_2$—O—$CH_2$—$CH_3$. It is preferably derived from polyethylene glycol. A general description is —$((CH_2)_a$—O$)_b$—H/$CH_3$, wherein a is a number from 1 to 6 and b is a number from 2 to 10.

$R_{100}$ and $R_{101}$ form together a mono or polycyclic heterocyclic ring.

A monocyclic or polycyclic ring may result in the structures 1C-. 1W as described above.

Preferably the monocyclic or polycyclic ring may result in a structure (B)

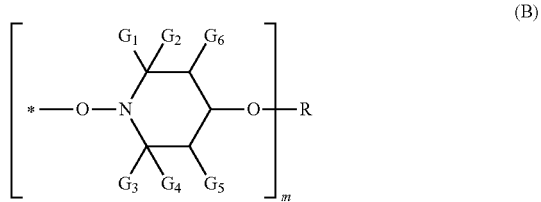

(B)

m is 1 to 4

R, if m is 1, is hydrogen, $C_1$-$C_{18}$alkyl which is uninterrupted or $C_2$-$C_{18}$alkyl which is interrupted by one or more oxygen atoms, cyanoethyl, benzoyl, glycidyl, a monovalent radical of an aliphatic carboxylic acid having 2 to 18 carbon atoms, of a cycloaliphatic carboxylic acid having 7 to 15 carbon atoms, of an α,β-unsaturated carboxylic acid having 3 to 5 carbon atoms or of an aromatic carboxylic acid having 7 to 15 carbon atoms, where each carboxylic acid can be substituted in the aliphatic, cycloaliphatic or aromatic moiety by 1 to 3-COO$Z_{12}$ groups, in which $Z_{12}$ is H, $C_1$-$C_{20}$alkyl, $C_3$-$C_{12}$alkenyl, $C_5$-$C_7$cycloalkyl, phenyl or benzyl; or R is a monovalent radical of a carbamic acid or phosphorus-containing acid or a monovalent silyl radical;

R, if m is 2, is $C_2$-$C_{12}$, $C_4$-$C_{12}$, xylylene, a divalent radical of an aliphatic dicarboxylic acid having 2 to 36 carbon atoms, of a cycloaliphatic or aromatic dicarboxylic acid having 8-14 carbon atoms or of an aliphatic, cycloaliphatic or aromatic dicarbamic acid having 8-14 carbon atoms, where each dicarboxylic acid may be substituted in the aliphatic, cycloaliphatic or aromatic moiety by one or two —COO$Z_{12}$ groups; or R is a divalent radical of a phosphorus-containing acid or a divalent silyl radical;

R, if m is 3, is a trivalent radical of an aliphatic, cycloaliphatic or aromatic tricarboxylic acid, which may be substituted in the aliphatic, cycloaliphatic or aromatic moiety by —COO$Z_{12}$, of an aromatic tricarbamic acid or of a phosphorus-containing acid, or is a trivalent silyl radical, R, if m is 4, is a tetravalent radical of an aliphatic, cycloaliphatic or aromatic tetracarboxylic acid;

$G_1$, $G_2$, $G_3$ and $G_4$ are independently of one another $C_1$-$C_4$alkyl, or $G_1$ and $G_2$ together and $G_3$ and $G_4$ together, or $G_1$ and $G_2$ together or $G_3$ and $G_4$ together are pentamethylene;

$G_5$ and $G_6$ are independently of one another hydrogen or $C_1$-$C_4$ alkyl;

A monocyclic or polycyclic ring may result in a structure (C)

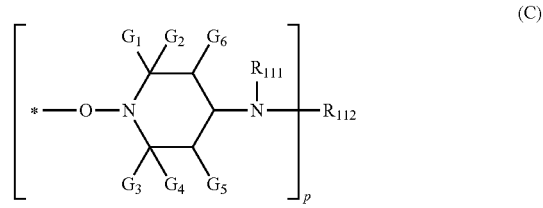

(C)

wherein X and $G_1$ to $G_6$ are as defined above;

p is 1, 2 or 3, $R_{111}$ is $C_1$-$C_{12}$alkyl, $C_5$-$C_7$cycloalkyl, $C_7$-$C_8$aralkyl, $C_2$-$C_{18}$alkanoyl, $C_3$-$C_5$alkenoyl or benzoyl;

$R_{112}$, if p is 1, is $C_1$-$C_{18}$alkyl, $C_5$-$C_7$cycloalkyl, $C_2$-$C_8$alkenyl unsubstituted or substituted by a cyano, carbonyl or carbamide group, or is glycidyl, a group of the formula —$CH_2CH(OH)$—Z or of the formula —CO—Z— or —CONH—Z wherein Z is hydrogen, methyl or phenyl; or $R_{101}$ and $R_{102}$ together when p is 1 can be the cyclic acyl radical of an aliphatic or aromatic 1,2- or 1,3-dicarboxylic acid;

$R_{112}$, if p is 2, is $C_2$-$C_{12}$, $C_6$-$C_{12}$arylene, xylylene, a —$CH_2CH(OH)CH_2$—O—B—O—$CH_2CH(OH)CH_2$— group, wherein B is $C_2$-$C_{10}$, $C_6$-$C_{15}$arylene or $C_6$-$C_{12}$cyclo; or, provided that $R_{101}$ is not alkanoyl, alkenoyl or benzoyl, $R_{102}$ can also be a divalent acyl radical of an aliphatic, cycloaliphatic or aromatic dicarboxylic acid or dicarbamic acid, or can be the group —CO—;

$R_{112}$ is a group

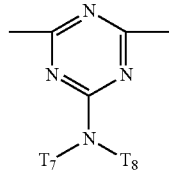

wherein $T_7$ and $T_8$ are independently hydrogen, $C_1$-$C_{18}$alkyl, or $T_7$ and $T_8$ together are $C_4$-$C_6$alkylene or 3-oxapentamethylene;

$R_{112}$, if p is 3, is 2,4,6-triazinyl;

Preparation of the Inventive Compounds of the Formula I

The compounds of the formula I with $R_{104}$=H are conveniently prepared via addition of hydroxylamines (II) to carbodiimides (III) according to the equation:

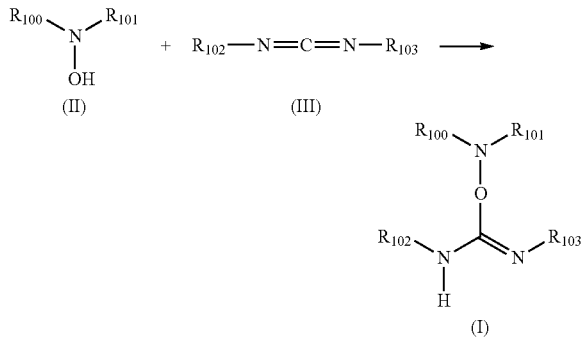

The addition can be conveniently performed by stirring the solution of (II) and (III) in an appropriate solvent such as for example ethyl acetate, toluene, dichloromethane, acetonitrile, tetrahydrofurane, hexane an the like. The reaction temperature can be room temperature (rt) or below, say −78° C. to room temperature or above, say rt to 150° C.

Admixture of catalysts, for example Broensted acids such as HCl, p-TsOH, $HBF_4$ or $H_2SO_4$ or Lewis acids such as for example $BF_3$ or $Cu(O_3SCF_3)$ or bases, e.g. alkali metal hydroxides, amides or hydrides may help improve the speed and yield of the addition of (II) to (III).

Thus, the invention further relates to a process to prepare a compound of the formula I

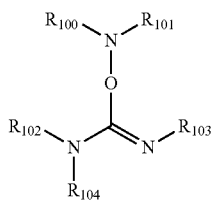

comprising the steps of
a) addition in a solvent of compound II

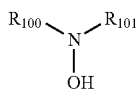

and compound III

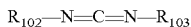

wherein $R_{100}$, $R_{101}$, $R_{102}$ and $R_{103}$ are as defined in claim 1, and b) optionally alkylation or acylation by adding $R_{104}$—X wherein $R_{104}$—X is either an alkylation agent comprising $C_1$-$C_{19}$alkyl-, $C_5$-$C_{12}$cycloalkyl-, $C_7$-$C_{10}$aralkyl-halides, -sulfonates, -trifluoromethansulfonates, or -trialkyloxonium salts; or $R_{104}$—X is an acylation agent comprising acyl halides or acylanhydrides.

The invention further relates to polymerisation initiators obtainable by a) addition in a solvent of compound II

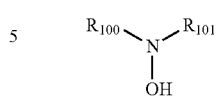

and compound III

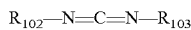

wherein $R_{100}$, $R_{101}$, $R_{102}$ and $R_{103}$ are as defined above, and b) optionally alkylation or acylation by adding $R_{104}$—X wherein $R_{104}$—X is either an alkylation agent comprising $C_1$-$C_{19}$alkyl-, $C_5$-$C_{12}$cycloalkyl-, $C_7$-$C_{10}$aralkyl-halides, -sulfonates, -trifluoromethansulfonates, or -trialkyloxonium salts; or R104-X is an acylation agent comprising acyl halides or acylanhydrides.

The hydroxylamines (II) and their preparation is well known. For example, Houben-Weyl E 16a describes on pages 296-310 syntheses of various hydroxylamines. A convenient synthesis method of hydroxylamines (II) consists of the reduction of the corresponding nitroxide radicals. The nitroxide radicals are known compounds and their preparation and reduction into the corresponding hydroxylamines is described for example in: L. B. Volodarsky, V. A. Reznikov, V. I. Ovcharenko, "Synthetic Chemistry of Stable Nitroxides" CRC Press, 1994.

Many carbodiimides (III) are commercially available, e.g.
N,N'-Dicyclohexylcarbodiimide
1,3-Diisopropylcarbodiimide
Bis-(o-tolyl)-carbodiimide
Bis-(p-tolyl)-carbodiimide
Bis-(2,6-diisopropylphenyl)-carbodiimide
Bis-(trimethylsilyl)-carbodiimide
1-sec-Butyl-3-ethylcarbodiimide
N-Cyclohexyl-N'[4-(dimethylamino)-α-naphthyl]-carbodiimide
1-Cyclohexyl-3-(2-morpholinoethyl)-carbodiimide
1,3-Di-tert-butylcarbodiimide
1-Ethyl-3-(3-dimethylaminopropyl)-carbodiimide
1-Ethyl-3-(3-dimethylaminopropyl)-carbodiimide methiodide
Poly-(1,3,5-triisopropylbenzene)-polycarbodiimide Methods for preparation of carbodiimides bearing another substituents are well-known and described for example in: Henri Ulrich, "Chemistry and technology of carbodiimides", Wiley 2007.

The compounds of the formula I where $R_{104}$ is not hydrogen are conveniently prepared via alkylation or acylation of the compounds of the formula I with $R_{104}$=H:

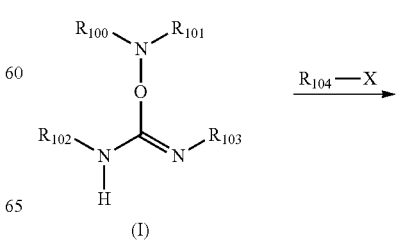

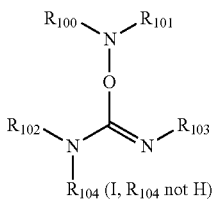

$R_{104}$ (I, $R_{104}$ not H)

The suitable alkylation agents $R_{104}$—X are well known and comprise e.g. alkyl-, cycloalkyl- or aralkyl halides, sulfonates, triflates or trialkyloxonium salts.

The suitable acylation agents $R_{104}$—X are well known and comprise e.g. acyl halides or acyl anhydrides.

The alkylation or acylation of compounds of the formula I ($R_{104}$=H) is optionally conducted in the presence of a base to neutralize the liberated acid H—X. Example of suitable bases are alkali hydroxides or alkali carbonates or amines such as triethylamine or pyridine.

Yet another possibility for the synthesis of the compounds of the formula I ($R_{104}$ not H) consists of reacting the carbodiimides (III) with alkylation or acylation agents to afford the carbodiimidium salts (IV) which are then submitted to reaction with the hydroxylamines (II) affording the desired compounds of the formula I.

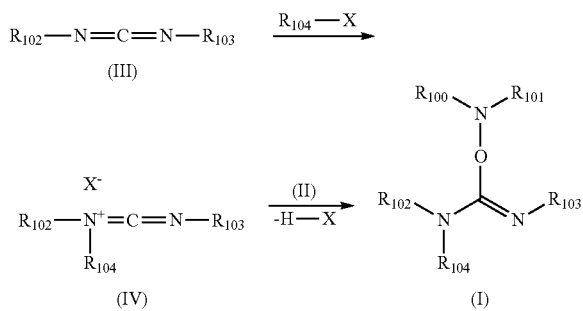

The synthesis of carbodiimidium salts (IV) is known. For example, R. Scheffold, E. Saladin; Angew. Chem. Int. Ed. 229, 11, (1972) describes the reaction of methyl iodide with dicyclohexylcarbodiimide to afford the corresponding carbodiimidium salt. Similar salts from carbodiimides and acyl chlorides are described by: K. Hartke, Angewandte Chemie, 214 (1962).

The compounds of formula I are present as polymerization auxiliaries or polymerization initiators in polymerizable compositions which comprise at least one ethylenically unsaturated, polymerizable monomer or oligomer. Preferably a coating is prepared.

The invention therefore further provides a composition comprising
A) at least one ethylenically unsaturated, polymerizable monomer or oligomer; and
B) at least one compound of the formula I.

In the composition, the component B) is present in a ratio to the component A) of from 0.01 to 30 mol %, preferably from 0.05 to 10 mol %, particularly preferably from 0.1 to 1.0 mol %.

Definition of the Ethylenically Unsaturated Compound:

The general radical-polymerizable compound is selected from known radical-polymerizable compounds having at least one ethylenically unsaturated double bond. Included are monomers, prepolymers, oligomers, a mixture thereof or a copolymer thereof.

Non-limiting examples of such monomers include: ethylenically unsaturated polymerizable monomers selected from the group consisting of alkenes, conjugated dienes, styrenes, acrolein, vinyl acetate, vinylpyrrolidone, vinylimidazole, maleic anhydride, acrylic acid, acrylic acid derivatives, vinyl halides and vinylidene halides.

Examples of alkenes and conjugated alkenes are ethylene, isoprene, 1,3-butadiene and $\alpha$-$C_5$-$C_{18}$alkenes.

Suitable styrenes may be substituted on the phenyl group by from one to three substituents selected from the group consisting of hydroxy, $C_1$-$C_4$alkoxy, e.g. methoxy or ethoxy, halogen, e.g. chlorine, amino and $C_1$-$C_4$alkyl, e.g. methyl or ethyl.

Unsaturated carboxylic acids such as (meth)acrylic acid, crotonic acid, itaconic acid (methylene succinic acid), maleic acid, or fumaric acid and salts, esters and amides thereof. Also mentioned are unsaturated fatty acids such as linolenic acid and oleic acid. Acrylic and methacrylic acid are preferred.

It is also possible, however, to use saturated di- or polycarboxylic acids in admixture with unsaturated carboxylic acids. Examples of suitable saturated di- or poly-carboxylic acids include, for example, malonic acid, succinic acid, glutaric acid, adipic acid, sebacic acid, 1,4-cyclohexane dicarboxylic acid, tetrachlorophthalic acid, tetrabromophthalic acid, phthalic anhydride, tetrahydrophthalic acid, isophthalic acid, terepthalic acid, trimellitic acid, heptanedicarboxylic acid, dodecanedicarboxylic acid, hexahydrophthalic acid, etc.

Esters of the above mentioned unsaturated acids are e.g. alkyl esters such as methyl, ethyl, 2-chloroethyl, N-dimethylaminoethyl, n-butyl, isobutyl-, pentyl, hexyl, cyclohexyl, 2-ethylhexyl, octyl, isobornyl [2-exobornyl]esters; or phenyl, benzyl or o-, m- and p-hydroxyphenyl esters; or hydroxy alkyl esters e.g. 2-hydroxyethyl, 2-hydroxypropyl, 4-hydroxybutyl, 3,4-dihydroxybutyl or glycerol [1,2,3-propanetriol]esters, or epoxy alkyl esters e.g. glycidyl, 2,3-epoxybutyl, 3,4-epoxy butyl, 2,3-epoxycyclohexyl, 10,11-epoxyundecyl esters, or amino alkyl or mercapto alkyl esters, or esters as described below.

Amides of the above mentioned unsaturated acids are e.g. (meth)acryl amides, N-substituted (meth)acryl amides, e.g. N-methylolacrylamide, N-methylolmethacrylamide, N-ethylacryamide, N-ethylmethacrylamide, N-hexylacrylamide, N-hexylmethacrylamide, N-cyclohexylacrylamide, N-cyclohexylmethacrylamide-, N-hydroxyethylacrylamide, N-phenylacrylamide, N-phenylmethacrylamide, N-benzylacrylamide, N-benzylmetacrylamide, N-nitrophenylacrylamide, N-nitrophenylmethacrylamide, N-ethyl-N-phenylacrylamide, N-ethyl-N-phenylmethacrylamide, N-(4-hydroxyphenyl)acrylamide, and N-(4-hydroxyphenyl)methacrylamide, IBMAA (N-isobutoxymethyl acrylamide, or amides with aliphatic polyvalent amines.
(Meth)acrylnitriles.

Unsaturated acid anhydrides such as itaconic anhydride, maleic anhydride, 2,3-dimethyl maleic anhydride, and 2-chloromaleic anhydride.

Styrenes, such as methyl styrene, chloromethyl styrene, and o-, m-, and p-hydroxystyrene. Vinyl ethers such as isobutyl vinyl ether, ethyl vinylether, 2-chloroethyl vinylether, hydroxyethyl vinylether, propyl vinylether, butyl vinylether, isobutyl vinyl ether, octyl vinylether and phenyl vinylether.

Vinyl esters such as vinyl acetate, vinyl chloroacetate, vinyl butyrate and vinyl benzoate. vinyl chloride and vinylidene chloride.

N-vinyl heterocyclic compounds, N-vinylpyrrolidone or suitably substituted vinylpyrrolidones, N-vinylcarbazol, 4-vinylpyridine, Further examples of esters are:
diacrylate esters such as 1,6-hexane diol diacrylate (HDDA), ethylene glycol diacrylate, propylene glycol diacrylate, tripropylene glycol diacrylate, neopentyl glycol diacrylate, hexamethylene glycol diacrylate and bisphenol A diacrylate, divinyl succinate, diallyl phthalate, triallyl phosphate, triallyl isocyanurate and tris(2-acryloylethyl) isocyanurate. trimethylolpropane triacrylate, trimethylolethane triacrylate, trimethylolpropane trimethacrylate, trimethylolethane trimethacrylate, tetramethylene glycol dimethacrylate, triethylene glycol dimethacrylate, tetraethylene glycol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol pentaacrylate, dipentaerythritol hexaacrylate, tripentaerythritol octaacrylate, pentaerythritol dimethacrylate, pentaerythritol trimethacrylate, dipentaerythritol dimethacrylate, dipentaerythritol tetramethacrylate, tripentaerythritol octamethacrylate, pentaerythritol diitaconate, dipentaerythritol trisitaconate, dipentaerythritol pentaitaconate, dipentaerythritol hexaitaconate, ethylene glycol diacrylate, 1,3-butanediol diacrylate, 1,3-butanediol dimethacrylate, 1,4-butanediol diitaconate, sorbitol triacrylate, sorbitol tetraacrylate, pentaerythritol-modified triacrylate, sorbitol tetramethacrylate, sorbitol pentaacrylate, sorbitol hexaacrylate, oligoester acrylates and methacrylates, glycerol di- and tri-acrylate, 1,4-cyclohexane diacrylate, bisacrylates and bismethacrylates of polyethylene glycol having a molecular weight of from 200 to 1500, and mixtures thereof. The following esters are also suitable: dipropylene glycol diacrylate, tripropylene glycol diacrylate, glycerol ethoxylate triacrylate, glycerol propoxylate triacrylate, trimethylolpropane ethoxylate triacrylate, trimethylolpropane propoxylate triacrylate, pentaerythritol ethoxylate tetraacrylate, pentaerythritol propoxylate triacrylate, pentaerythritol propoxylate tetraacrylate, neopentyl glycol ethoxylate diacrylate, neopentyl glycol propoxylate diacrylate.

Non limiting examples of higher molecular weight (oligomeric) polyunsaturated compounds (also known as prepolymers) are esters of ethylenically unsaturated mono- or polyfunctional carboxylic acids as described above and polyols or polyepoxides, and polymers having ethylenically unsaturated groups in the chain or in side groups, e.g. unsaturated polyesters, polyamides and polyurethanes and copolymers thereof, alkyd resins; polybutadiene and butadiene copolymers, polyisoprene and isoprene copolymers, polymers and copolymers having (meth)acrylic groups in side chains such as methacrylated urethanes and also mixtures of one or more such polymers.

Suitable polyols are aromatic and, especially, aliphatic and cycloaliphatic polyols. Examples of aromatic polyols are benzyl alcohol, hydroquinone, 4,4'-dihydroxydiphenyl, 2,2-di(4-hydroxyphenyl)propane, and novolaks and resols. Examples of polyepoxides are those based on the said polyols, especially the aromatic polyols and epichlorohydrin. Also suitable as polyols are polymers and copolymers that contain hydroxyl groups in the polymer chain or in side groups, e.g. polyvinyl alcohol and copolymers thereof or polymethacrylic acid hydroxyalkyl esters or copolymers thereof. Further suitable polyols are oligoesters having hydroxyl terminal groups.

Examples of aliphatic and cycloaliphatic polyols include alkylenediols having preferably from 2 to 12 carbon atoms, such as ethylene glycol, 1,2- or 1,3-propanediol, 1,2-, 1,3- or 1,4-butanediol, pentanediol, hexanediol, octanediol, dodecanediol, diethylene glycol, triethylene glycol, polyethylene glycols having molecular weights of preferably from 200 to 1500, 1,3-cyclopentanediol, 1,2-, 1,3- or 1,4-cyclohexanediol, 1,4-dihydroxymethylcyclohexane, glycerol, tris(β-hydroxyethyl)amine, trimethylolethane, trimethylolpropane, pentaerythritol, dipentaerythritol and sorbitol.

The polyols may be partially or fully esterified by one or by different unsaturated carboxylic acid(s), it being possible for the free hydroxyl groups in partial esters to be modified, for example etherified, or esterified by other carboxylic acids.

A second oligomer used in combination with a monomer is an acrylate which has been modified by reaction with primary or secondary amines, as described, for example, in U.S. Pat. No. 3,844,916 of Gaske, in EP 280 222 of Weiss et al., in U.S. Pat. No. 5,482,649 of Meixner et al. or in U.S. Pat. No. 5,734,002 of Reich et al. Such amine-modified acrylates are also termed aminoacrylates. Aminoacrylates are obtainable, for example, under the name EBECRYL 80, EBECRYL 81, EBECRYL 83, EBECRYL P115, EBECRYL 7100 from UCB Chemicals, under the name Laromer PO 83F, Laromer PO 84F, Laromer PO 94F from BASF, under the name PHOTOMER 4775 F, PHOTOMER 4967 F from Cognis or under the name CN501, CN503, CN550 from Cray Valley.

The unsaturated polymer can be used alone or in any desired mixtures.

Preparation of the Coating

The components of the formulation and optionally further additives are applied uniformly to a substrate by means of known coating techniques, for example by spin-coating, immersion, knife coating, curtain pouring, brush application or spraying, especially by electrostatic spraying and reverse-roll coating, and also by electrophoretic deposition. The quantity applied (coat thickness) and the nature of the substrate (layer support) are dependent on the desired field of application. The range of coat thicknesses generally comprises values from 0.1 μm to more than 300 μm.

Substrates

Suitable are substrates of all kinds, e.g. wood, textiles, paper, ceramics, glass, glass fibres, plastics such as polyester, polyethylene terephthalate, polyolefins or cellulose acetate, especially in the form of films, and also for metals such as Al, Cu, Ni, Fe, Zn, Mg or Co and GaAs, Si or $SiO_2$, to which there is to be applied a protective layer or an image by image-wise exposure.

Applications:

Liquid coating or powder coating or gelcoats. The coatings may be pigmented. Also possible is the use in printing inks.

The above-described compositions may further comprise customary additives, which may, as an alternative, also be added after the polymerization. Such additives can be added in small amounts, e.g. UV-absorbers or light stabilizers, e.g. compounds selected from the group consisting of hydroxyphenylbenzotriazoles, hydroxyphenylbenzophenones, oxalamides and hydroxyphenyl-s-triazines. Particularly suitable light stabilizers are those selected from the group consisting of sterically hindered amines (HALS), e.g. of the 2-(2-hydroxyphenyl)-1,3,5-triazine or 2-hydroxyphenyl-2H-benzotriazole type. Examples of light stabilizers of the 2-(2-hydroxyphenyl)-1,3,5-triazine type are known from the patent literature, e.g. U.S. Pat. No. 4,619,956, EP-A-434 608, U.S. Pat. No. 5,198,498, U.S. Pat. No. 5,322,868, U.S. Pat. No. 5,369,140, U.S. Pat. No. 5,298,067, WO-94/18278, EP-A-704 437, GB-A-2,297,091 or WO-96/28431.

The compositions may further comprise other customary additives, e.g. fillers such as calcium carbonate, silicates, glass or glass fibre material, talcum, kaolin, mica, barium sulphate, metal oxides and hydroxides, carbon black, graphite, pulverized wood and pulverized or fibrous material from other natural products, synthetic fibres, plasticizers, lubricants, emulsifiers, pigments, fluidizers, catalysts, optical brighteners, flame retardants, antistatics or blowing agents.

The invention further provides a process for preparing the above-described oligomer, cooligomer, polymer or copolymer by free-radical polymerization using the above-described novel compounds of formula I.

Free radical polymerisation includes thermal polymerisation and/or UV polymerisation. Thermal polymerisation is thermal curing, IR-curing or NIR-curing Thermal Curing:

Thermal curing refers to the application of convection heat or IR- or NIR-radiation after the mixture has been applied to substrate. In case of powder coatings the adhered powder coating is first melted to form a surface layer preferably by convection heat.

NIR-Curing

The NIR radiation used in the process according to the invention is short-wave infrared radiation in the wavelength range from about 750 nm to about 1500 nm, preferably 750 nm to 1200 nm. Radiation sources for NIR radiation include, for example, conventional NIR radiation emitters, which are available commercially (for example, from Adphos).

IR-Curing

The IR radiation used in the process according to the invention is medium wave radiation in the wave length range from about 1500 nm to about 3000 nm and/or longer-wave infrared radiation in the wave length range above 3000 nm.

IR radiation emitters of this kind are available commercially (for example, from Heraeus).

The invention further provides a generally applicable, inventive process for controlled degradation of polyolefins so to say lowering the molecular weight of polypropylene, propylene copolymers or polypropylene blends using the above-described novel compounds of formula I.

In the process for reducing the molecular weight (degradation process), the above-described compounds of the formula I are present in concentrations, based on the amount of polymers to be degraded, of from about 0.001 to 5.0% by weight, in particular from 0.01 to 2.0% by weight and particularly preferably from 0.02 to 1.0% by weight. The compounds of the formula I can be added as individual compounds or as mixtures to the polymer to be degraded.

The polypropylene-type polymers to be degraded can encompass propylene homopolymers, propylene copolymers and polypropylene blends. Propylene copolymers may contain various proportions up to 90%, preferably up to 50%, of comonomers. Examples of comonomers are: olefins such as 1-olefins, e.g. ethylene, 1-butene, 1-pentene, 1-hexene, 1-heptene or 1-octene, isobutylene, cycloolefins, e.g. cyclopentene, cyclohexene, norbornene or ethylidenenorborne, dienes such as butadiene, isoprene, 1,4-hexadiene, cyclopentadiene, dicyclopentadiene or norbornadiene; also acrylic acid derivatives and unsaturated carboxylic anhydrides such as maleic anhydride.

Polypropylene blends which can be used are mixtures of polypropylene with polyolefins. Examples are blends of polypropylene with polyethylene selected from the group consisting of high density polyethylene (HDPE), high molecular weight high density polyethylene (HMW HDPE), ultra high molecular weight high density polyethylene (UHMW HDPE), medium density polyethylene (MDPE), low density polyethylene (LDPE), linear low density polyethylene (LLDPE), branched low density polyethylene (BLDPE) and ethylene-propylenediene terpolymers (EPDM) containing small proportions of diene.

Incorporation into the polymers can be carried out, for example, by mixing the above-described compounds I or mixtures thereof and, if desired, further additives into the polymers using the methods customary in process technology.

Incorporation can, alternatively, also be carried out at temperatures which do not yet cause decomposition of the polymers (latent compound). The polymers prepared in this way can subsequently be heated a second time and subjected to an elevated temperature for a sufficient period of time so that the desired polymer degradation occurs.

PREPARATION EXAMPLES

The following Table 1 summarizes the prepared compounds

TABLE 1

Examples of synthesized compounds of the formula (I)

| Nr | Structure |
|---|---|
| 1 | (structure) |
| 2 | (structure) |

TABLE 1-continued

Examples of synthesized compounds of the formula (I)

| Nr | Structure |
|---|---|
| 3 | (structure) |
| 4 | (structure) |
| 5 | (structure) |
| 6 | (structure) |
| 7 | (structure) |
| 8 | (structure) |
| 9 | (structure) |

TABLE 1-continued

Examples of synthesized compounds of the formula (I)

| Nr | Structure |
|----|-----------|
| 10 | (structure) |
| 11 | (structure) |
| 12 | (structure) |
| 13 | (structure) |
| 14 | (structure) |
| 15 | (structure) |

Example 1

Preparation of acetic acid 1-(N,N'-dicyclohexyl-carbamimidoyloxy)-2,2,6,6-tetramethyl-piperidin-4-yl ester (compound 1)

Prepartion of 4-acetoxy-1-hydroxy-2,2,6,6-tetramethylpiperidine

4-Acetoxy-2,2,6,6-tetramethylpiperidine-N-oxyl (214.3 g, 1 mol) is dissolved in methanol (500 ml). Aqueous hydroxylamine (92.5 g of a 50% solution in water, 1.4 mol) is added over 10 minutes and the solution is then refluxed for one hour under argon. The colorless solution is evaporated and the solid residue is dried at 65° C./0.1 mbar until constant weight to afford 214.95 g of the title compound as a colorless solid.

To a solution of 4-acetoxy-1-hydroxy-2,2,6,6-tetramethylpiperidine (214.95 g, 0.998 mol) in tetrahydrofuran (1000 ml) is added dicyclohexylcarbodiimide (212.5 g, 1.03 mol) and the solution is heated to 65° C. under argon for 21 h. The reaction mixture is evaporated and the solid is recrystallized from acetonitrile to afford 295.7 g of the compound (I) as a colorless powder, m.p. 63-73° C.

For $C_{24}H_{43}N_3O_3$ (421.63) calculated/found (%): C, 68.37/68.26; H, 10.28/10.29; N, 9.97/10.04.

$^1$H-NMR (CDCl$_3$, 300 MHz): 5.4-5.3 (d, 1H, NH), 5.13-5.02 (m, 1H, CH-OAc), 3.6-3.4 (m, 2H, 2x>N—CH<(CH$_2$)$_5$), 2.03 (s, 3H, OCOCH$_3$), 2.1-1.0 (m, 36H, residual aliphatic H)

Example 2

Preparation of acetic acid 1-(N,N'-dicyclohexyl-carbamimidoyloxy)-2,6-diethyl-2,3,6-trimethyl-piperidin-4-yl ester (compound 2)

4-Acetoxy-2,6-diethyl-2,3,6-trimethylpiperidine-N-oxyl (4.04 g, 15.76 mmol, prepared as described by Fischer, Hanns; Kramer, Andreas; Marque, Sylvain R. A.; Nesvadba, Peter.: Macromolecules (2005), 38(24), 9974-9984) is dissolved in THF (20 ml) and hydrogenated in the presence of 0.38 g Pt (5% on carbon) catalyst using 4 bar hydrogen pressure. The hydrogen uptake stops after approx. one hour. To the filtered reaction solution is added sodium hydride catalyst (35 mg, 55% dispersion in a mineral oil) and dicyclohexylcarbodiimide (3.3 g, 16 mmol). The mixture is then stirred for 17 hours at 60° C. under argon, then evaporated and chromatographed on silica gel with $CH_2Cl_2$-EtOAc-MeOH (2:2:1) to afford 0.95 g of the title compound as a colorless oil.

$^1$H-NMR ($CDCl_3$, 300 MHz): 5.4-4.9 (m, 2H, NH and >CH-OAc), 3.6-3.4 (m, 2H, 2x>N—CH<$(CH_2)_5$), 2.05 (s, 3H, $\overline{O}COCH_3$), 2.1-0.7 (m, 42H, residual aliphatic H)

Example 3

Preparation of acetic acid 1-(N-acetyl-N,N'-dicyclohexyl-carbamimidoyloxy)-2,2,6,6-tetramethyl-piperidin-4-yl ester (compound 3)

To a solution of compound 1 (4.21 g, 10 mmol) [prepared according to Example 1] in toluene (25 ml) is added triethylamine (1.55 ml, 11 mmol) and acetyl chloride (0.78 ml, 11 mmol). The mixture is stirred at room temperature for 7 hours, then washed with water (2×10 ml), dried over $MgSO_4$ and evaporated. The residue is chromatographed over silica gel with hexane-ethyl acetate (4:1) and the pure fractions are recristallized from pentane to afford 1.05 g of the title compound as a white solid, mp. 125-130° C.

For $C_{26}H_{45}N_3O_4$ (463.47) calculated/found (%): C, 67.35/67.33; H, 9.78/9.74; N, 9.06/9.00.

$^1$H-NMR ($CDCl_3$, 300 MHz): 5.1-5.0 (m, 1H, >CH-OAc), 3.6-2.9 (m, 2H, 2x>N—CH<$(CH_2)_5$), 2.04 (s, 3H, $COCH_3$), 2.02 (s, 3H, $COCH_3$), 2.4-1.1 (m, 36H).

Example 4

Preparation of acetic acid 1-(N,N'-dicyclohexyl-N-octadecanoyl-carbamimidoyloxy)-2,2,6,6-tetramethyl-piperidin-4-yl ester (compound 4)

To a solution of compound 1 (4.21 g, 10 mmol) [prepared according to Example 1] in toluene (25 ml) is added triethylamine (1.46 ml, 10.5 mmol) and stearoyl chloride (3.2 g, 10.5 mmol). The mixture is stirred at room temperature for 30 minutes and then additional triethylamine (1.46 ml, 10.5 mmol) and stearoyl chloride (3.2 g, 10.5 mmol) is added. The suspension is stirred at room temperature for 18 hours, then evaporated and chromatographed over silica gel with hexane-ethyl acetate (9:1) to afford 4.03 g of the title compound as a colorless oil.

For $C_{42}H_{77}N_3O_4$ (688.10) calculated/found (%): C, 73.31/73.11; H, 11.28/11.00; N, 6.11/6.01.

$^1$H-NMR ($CDCl_3$, 300 MHz): 5.09-5.02 (m, 1H, >CH-OAc), 3.3-3.2 (m, 2H, 2x>N—CH<$(CH_2)_5$), 2.03 (s, 3H, $\overline{O}COCH_3$), 2.4-0.8 (m, 68H, residual aliphatic H), 0.90-0.86 (t, 3H, $CO(CH_{12})_{16}$—$C\underline{H}_3$)

Example 5

Preparation of acetic acid 1-(N-benzoyl-N,N'-dicyclohexyl-carbamimidoyloxy)-2,2,6,6-tetramethyl-piperidin-4-yl ester (compound 5)

To a solution of compound 1 (4.21 g, 10 mmol) [prepared according to Example 1] in toluene (25 ml) is added triethylamine (1.55 ml, 11 mmol) and benzoyl chloride (1.55 g, 11 mmol). The mixture is stirred at room temperature for 24 hours, then washed with water (2×10 ml), dried over $MgSO_4$ and evaporated. The residue is chromatographed over silica gel with hexane-ethyl acetate (4:1) and the pure fractions are recristallized from acetonitrile to afford 0.98 g of the title compound as a white solid, mp. 147-152° C.

Mass spectrum: for $C_{31}H_{47}N_3O_4$ (525.74) calculated M=525.74. Found M=525.3.

$^1$H-NMR ($CDCl_3$, 300 MHz): 7.5-7.2 (m, 5H, $C_6H_5$), 5.04-4.97 (m, 1H, >CH-OAc), 3.5-3.3 (m, 2H, 2x>N—CH<$(CH_2)_5$), 2.04 (s, 3H, $0COCH_3$), 2.1-0.9 (m, 36H, residual aliphatic H).

Example 6

Preparation of benzoic acid 1-(N,N'-dicyclohexyl-carbamimidoyloxy)-2,2,6,6-tetramethyl-piperidin-4-yl ester (compound 6)

4-Benzoyloxy-2,2,6,6-tetramethylpiperidine-N-oxyl (30.0 g, 109 mmol) is dissolved in THF (100 ml) and hydrogenated in the presence of 0.65 g Pt (5% on carbon) catalyst using 4 bar hydrogen pressure. The hydrogen uptake stops after approximately one hour. The reaction solution is filtered and evaporated to afford 31.65 g of the corresponding hydroxylamine as a white solid. An aliquot of this material (27.75 g, 100 mmol) and dicyclohexylcarbodiimide (21.6 g, 105 mmol) is dissolved in THF (200 ml) and the mixture is stirred at 50° C. for 22 hours under argon, then evaporated and chromatographed on silica gel with hexane-ethyl acetate (9:1) and then ethyl acetate-acetone (1:1). The pure fractions are recrystallized from acetonitrile to afford 24.4 g of the title compound as a colorless solid, mp. 50-57° C.

For $C_{29}H_{45}N_3O_3$ (483.70) calculated/found (%): C, 72.01/71.63; H, 9.38/9.44; N, 8.69/8.63.

$^1$H-NMR ($CDCl_3$, 300 MHz): 8.04-8.01 (m, 2ArH), 7.59-7.42 (m, 3 ArH), 5.47-5.29 (m, 2H, NH and >CH—OBz), 3.55-3.45 (m, 2H, 2x>N—CH<$(CH_2)_5$), 2.2-1.05 (m, 36H, residual aliphatic H).

Example 7

Preparation of benzoic acid 1-(N,N'-di-p-tolyl-carbamimidoyloxy)-2,2,6,6-tetramethyl-piperidin-4-yl ester (compound 7)

1-Hydroxy-4-benzoyloxy-2,2,6,6-tetramethylpiperidine (5.75 g, 20.7 mmol) [prepared as described in Example 6] and di-p-tolylcarbodiimide (4.8 g, 21.6 mmol) are dissolved in THF (40 ml) and the solution is stirred at room temperature for 17 hours. The solvent is evaporated and the residue is chromatographed on silica gel with hexane-ethyl acetate (9:1). The pure fractions are recrystallized from acetonitrile to afford 6.55 g of the title compound as a colorless solid, mp. 124-128° C.

For $C_{31}H_{37}N_3O_3$ (499.66) calculated/found (%): C, 74.52/74.40; H, 7.46/7.50; N, 8.41/8.42.

$^1$H-NMR (CDCl$_3$, 300 MHz): 8.25-8.21 (bs, NH), 8.04-6.93 (m, 13ArH), 5.37-5.26 (m, 1H, >CH—OBz), 2.31 (s, 2×CH$_3$), 2.18-1.35 (m, 2×CH$_2$), 1.26 (s, 2×CH$_3$), 1.22 (s, 2×CH$_3$).

Example 8

Preparation of 1,3-dicyclohexyl-2-(4-hydroxy-2,2,6,6-tetramethyl-piperidin-1-yl)-isourea (compound 8)

4-Hydroxy-2,2,6,6-tetramethylpiperidine-N-oxyl (17.25 g, 100 mmol) is dissolved in THF (100 ml) and hydrogenated in the presence of 0.35 g Pt (5% on carbon) catalyst using 4 bar hydrogen pressure. The hydrogen uptake stops after approximately one hour. The reaction mixture is then filtered and mixed with the solution of dicyclohexylcarbodiimide (21.15 g, 102.5 mmol). The solution is then heated under argon at 60° C. for 17 hours, concentrated, diluted with ethyl acetate (40 ml) and allowed to crystallize. The crystals are filtered off, washed with cold ethyl acetate and dried to afford 34.03 g of the title compound as a colorless solid, mp. 157-161° C.

For C$_{22}$H$_{41}$N$_3$O$_2$ (379.59) calculated/found (%): C, 69.61/69.29; H, 10.89/10.60; N, 11.07/11.17.

$^1$H-NMR (CDCl$_3$, 300 MHz): 5.44-5.41 (bd, NH), 4.09-4.00 (m, 1H, >CH—OH), 3.51-3.44 (m, 2H, 2x>N—CH<(CH$_2$)$_5$), 2.14-0.99 (m, 25H, residual aliphatic H), 1.25 (s, 2×CH$_3$), 1.11 (s, 2×CH$_3$). The structure of compound 8 is confirmed by X-ray analysis of crystals grown from dichloromethane-ethanol.

Example 9

Preparation of 2-(4-hydroxy-2,2,6,6-tetramethyl-piperidin-1-yl)-1,3-diisopropyl-isourea (compound 9)

4-Hydroxy-2,2,6,6-tetramethylpiperidine-N-oxyl (17.25 g, 100 mmol) is dissolved in THF (100 ml) and hydrogenated in the presence of 0.35 g Pt (5% on carbon) catalyst using 4 bar hydrogen pressure. The hydrogen uptake stops after approximately one hour. The reaction mixture is then filtered and mixed with the solution of diisopropylcarbodiimide (18.6 ml, 120 mmol). The solution is then heated under argon at 55° C. for 6 hours, concentrated, diluted with ethyl acetate (40 ml) and allowed to crystallize. The crystals are filtered off, washed with cold ethyl acetate and dried to afford 25.8 g of the title compound as a colorless solid, mp. 118-123° C.

$^1$H-NMR (CDCl$_3$, 300 MHz): 5.36-5.33 (bd, NH), 4.07-3.76 (m, 3H, >CH—OH, 2x>N—CH(CH$_3$)$_2$), 1.96-1.49 (m, 4H), 1.32 (s, 2×CH$_3$), 1.19 (s, 2×CH$_3$), 1.12-1.10 (d, 12H, 2x—CH(CH$_3$)$_2$).

Example 10

Preparation of acetic acid 1-[N,N'-bis(2,6-diisopropyl-phenyl)-carbamimidoyloxy]-2,2,6,6-tetramethyl-piperidin-4-yl ester (compound 10)

To a solution of 4-acetoxy-1-hydroxy-2,2,6,6-tetramethylpiperidine (2.63 g, 12.2 mmol, [prepared as described in Example 1] in tetrahydrofuran (10 ml) is added bis(2,6-diisopropylphenyl)carbodiimide (4.52 g, 12.5 mmol) and the solution is heated to 52° C. under argon for 20 hours. The reaction mixture is evaporated and the residue chromatographed on silica gel with hexane-ethylacetate (5:1). The pure fractions are recrystallized from hexane to afford 1.87 g of the compound 10 as colorless crystals, mp. 144-147° C.

$^1$H-NMR (CDCl$_3$, 300 MHz): 7.3-6.8 (m, 6 ArH), 5.05-4.96 (m, 1H, >CH-OAc), 3.51-3.42 (m, 2H, CHMe$_2$), 3.24-3.17 (m, 2H, CHMe$_2$), 2.01 (s, 3H, OCOCH$_3$), 2.0-1.50 (m, 4H, 2×CH$_2$), 1.43 (s, 6H, 2×CH$_3$), 1.25 (d, J=6.9 Hz, 24H, 8×CH$_3$), 1.07 (s, 6H, 2×CH$_3$).

Example 11

Preparation of 1,3-bis(2,6-diisopropyl-phenyl)-2-(4-hydroxy-2,2,6,6-tetramethylpiperidin-1-yl)-isourea (compound 11)

4-Hydroxy-2,2,6,6-tetramethylpiperidine-N-oxyl (5.16 g, 30 mmol) is dissolved in THF (40 ml) and hydrogenated in the presence of 0.08 g Pt (5% on carbon) catalyst using 4 bar hydrogen pressure. The hydrogen uptake stops after approximately one hour. The reaction mixture is then filtered and mixed with the solution of bis(2,6-diisopropylphenyl)carbodiimide (3.8 g, 10.5 mmol) in THF (30 ml). The solution is heated under argon at 55° C. for 6 hours, concentrated, the residue dissolved in dichloromethane (70 ml), washed with water (2×20 ml) and concentrated again. The residue is recrystallized from dichloromethane-ethyl acetate to afford 3.28 g of the title compound as a colorless solid, mp. 174-176° C.

$^1$H-NMR (CDCl$_3$, 300 MHz): 7.3-6.8 (m, 6 ArH), 4.04-3.95 (m, 1H, >CH—OH), 3.52-3.42 (m, 2H, CHMe$_2$), 3.27-3.18 (m, 2H, CHMe$_2$), 2.0-1.40 (m, 4H, 2×CH$_2$), 1.43 (s, 6H, 2×CH$_3$), 1.27 (d, J=6.9 Hz, 24H, 8×CH$_3$), 1.03 (s, 6H, 2×CH$_3$).

Example 12

Preparation of 2-(4-hydroxy-2,2,6,6-tetramethyl-piperidin-1-yl)-1,3-di-p-tolyl-isourea (compound 12)

4-Hydroxy-2,2,6,6-tetramethylpiperidine-N-oxyl (1.9 g, 11 mmol) is dissolved in THF (40 ml) and hydrogenated in the presence of 0.035 g Pt (5% on carbon) catalyst using 4 bar hydrogen pressure. The hydrogen uptake stops after approximately one hour. The reaction mixture is then filtered and mixed with the solution of bis-p-tolyl-carbodiimide (2.45 g, 11 mmol) in THF (30 ml). The solution is stirred under argon at room temperature for 16 hours and concentrated. The residue is chromatographed on silica gel with hexane-ethyl acetate (1:1) and the pure fractions are crystallized from ethyl acetate to afford 1.6 g of the title compound as a colorless solid, mp. 124-126° C.

$^1$H-NMR (CDCl$_3$, 300 MHz): 8.2-6.9 (m, 8 ArH), 4.15-3.9 (m, 1H, >CH—OH), 2.3 (s, 6H, 2×CH$_3$), 2.0-1.40 (m, 4H, 2×CH$_2$), 1.21 (s, 6H, 2×CH$_3$), 1.12 (s, 6H, 2×CH$_3$).

Example 13

Preparation of 1,3-dicyclohexyl-2-diethylamino-isourea (compound 13)

To a solution of dicyclohexylcarbodiimide (10.3 g, 50 mmol) and N,N-diethylhydroxylamine (6.7 g, 75 mmol) in THF (30 ml) is added finely powdered NaOH (0.2 g) and the mixture is stirred at room temperature for 50 hours. The reaction mixture is then filtered and the filtrate is evaporated on the rotary evaporator below 45° C. to afford 13.24 g of the title compound as a light yellow oil.

ESI-MS: for C$_{17}$H$_{33}$N$_3$O (295.47) found MH$^+$=296.

¹H-NMR (CDCl₃, 300 MHz): 3.6-3.4 (m, 2H, 2x>N—CH<(CH₂)₅), 2.82 (q, J=6.9 Hz, 4H, 2×CH₂), 2.1-1.0 (m, 20H, residual aliphatic H), 1.1 (t, J=6.9 Hz, 6H, 2×CH₃).

Example 14

Preparation of 1,3-Bis-(2,6-diisopropyl-phenyl)-2-diethylamino-isourea (compound 14)

To a solution of bis(2,6-diisopropylphenyl)carbodiimide (4.35 g, 12 mmol) and N,N-diethylhydroxylamine (1.6 g, 18 mmol) in THF (20 ml) is added finely powdered NaOH (48 mg) and the mixture is stirred at room temperature for 22 hours. The reaction mixture is then filtered and the filtrate is evaporated on the rotary evaporator below 45° C. The residue is recrystallized twice from acetonitrile to afford 1.75 g of the title compound as a white solid, mp. 113-116° C.

APCI-MS: for C₂₉H₄₅N₃O (451.70) found MH⁺=452.44.

¹H-NMR (CDCl₃, 300 MHz): 7.3-6.8 (m, 6 ArH), 3.6-3.4 (m, 2H, CHMe₂), 3.2-3.05 (m, 2H, CHMe₂), 3.0-2.8 (m, 4H, 2×CH₂), 1.5-0.9 (30H, 10×CH₃).

Example 15

Preparation of decanedioic acid bis[1-(N,N'-dicyclohexyl-carbamimidoyloxy)-2,2,6,6-tetramethyl-piperidin-4-yl]ester (compound 15)

To a solution of 1,3-dicyclohexyl-2-(4-hydroxy-2,2,6,6-tetramethyl-piperidin-1-yl)-isourea [compound 8 prepared according to Example 8] (8.35 g, 22 mmol) and 4-dimethylaminopyridine (160 mg) in pyridine (20 ml) is added sebacoylchloride (2.5 g, 10.5 mmol). The mixture is stirred at room temperature for 22 hours and then diluted with ice-water (250 ml). The precipitate is filtered off, washed with water and dried to afford 9.75 g of the title compound as an off-white solid.

APCI-MS: for C₅₄H₉₆N₆O₆ (925.4) found MH⁺=925.3.

¹H-NMR (CDCl₃, 300 MHz): 5.1-4.9 (m, 2H, >CH—OCO—), 3.6-3.4 (m, 4H, 4x>N—CH<(CH₂)₅), 2.27 (t, J=6 Hz, 4H, 2×CH₂), 2.0-1.0 (m, 84H, residual aliphatic H).

Polymerization Examples Using Selected Compounds from Table 1

1. Bulk Polymerization of Pure Monomers: Materials and Methods:
- All monomers are distilled under argon or under reduced pressure via a Vigreux column shortly before use.
- All reaction mixtures are freed of oxygen by purging with argon using the freeze/thaw technique and subsequently maintained under argon gas prior to the polymerization.
- The reactants are in the form of a clear homogeneous solution before commencement of the polymerization reaction.
- The monomer conversion is determined via ¹H-NMR by integrating the signals of the polymer and unreacted monomer.
- The polymers are characterized by GPC (gel permeation chromatography).
- GPC: a two-piston production model pump RHEOS 4000 from FLUX INSTRUMENTS (represented by Ercatech AG, Bern, Switzerland) is used. The pump output is 1 ml/min. The chromatography is carried out on two Plgel 5 µm mixed-C columns from POLYMER INSTRUMENTS, Shropshire UK connected in series at 40° C. in THF. These columns are calibrated using polystyrene having $M_n$ values in the range from 200 to 2 000 000. The fractions are measured using an RI detector ERC-7515A from ERCATECH AG at 30° C.

Example 100

Polymerization of n-butyl Acrylate Using Compound 1 (Table 1) at 120° C.

421 mg (1 mmol) of the compound 1 (Table 1) and 12.82 g (100 mmol) of n-butyl acrylate are placed in a 50 ml three-necked round-bottom flask provided with thermometer, condenser and magnetic stirrer and the mixture is degassed. The clear solution is heated at 120° C. for 5 hours under argon and then cooled to room temperature to afford a colorless, viscous polymer. Conversion of the monomer=91° A, GPC: $M_n$=3243, $M_w$=135806.

Example 101

Polymerization of tert-butyl Acrylate Using the Compound 1 (Table 1) at 100° C.

421 mg (1 mmol) of the compound 1 (Table 1) and 12.82 g (100 mmol) of tert-butyl acrylate are placed in a 50 ml three-necked round-bottom flask provided with thermometer, condenser and magnetic stirrer and the mixture is degassed. The clear solution is heated at 100° C. for 5 hours under argon and then cooled to room temperature to afford a colorless, glassy polymer. Conversion of the monomer=84%, GPC: $M_n$=16909, $M_w$=172366.

Example 102

Polymerization of n-butyl Acrylate Using the Compound 3 (Table 1) at 80° C.

150 mg (0.324 mmol) of the compound 3 (Table 1) and 4.15 g (32.3 mmol) of n-butyl acrylate are placed in a 10 ml three-necked round-bottom flask provided with thermometer, condenser and magnetic stirrer and the mixture is degassed. The clear solution is heated at 80° C. for 5 hours under argon and then cooled to room temperature to afford a colorless, glassy polymer. Conversion=80%, GPC: $M_n$=330607, $M_w$=634265.

Example 103

Polymerization of n-butyl Acrylate Using the Compound 13 (Table 1) at 120° C.

148 mg (0.5 mmol) of the compound 13 (Table 1) and 6.43 g (50 mmol) of n-butyl acrylate are placed in a 10 ml three-necked round-bottom flask provided with thermometer, condenser and magnetic stirrer and the mixture is degassed. The clear solution is heated at 120° C. for 5 hours under argon and then cooled to room temperature to afford a colorless, glassy polymer. Conversion=76%, GPC: $M_n$=6997, $M_w$=80251.

2. Polymerization of a Coating Composition

The following composition is used (w/w %)

| | |
|---|---|
| Urethane-acrylate (Ebecryl 4858, UCB Chemicals/Cytec) | 50% |
| 1,6-Hexandiol diacrylate (UCB Chemicals/Cytec) | 30% |
| Tripropylene glycol diacrylate (UCB Chemicals/Cytec) | 20% |

1% of a compound from Table 1 is dissolved in this composition and the resulting mixture is submitted to Differential scanning calorimetry (DSC) measurement. The activity of the tested compound is manifested by the exothermic curing reaction which is characterized by the Onset, Peak and Endset temperatures as well as the amount of heat liberated (exothermy).

The following DSC parameters are used:
Apparatus: DSC 30 (Mettler)
Temperature Gradient: 5° C./Min
Temperature Range: 30-300° C.
Measurement under nitrogen, flow rate 5 ml/Min
Sample amount: approx. 10 mg compound in an aluminum cup The results summarized in the Table 2 show that no curing occurs with the blank formulation but that distinct exothermic curing is observed with the examples of the inventive compounds.

TABLE 2

| | DSC evaluation | | | |
|---|---|---|---|---|
| Compound | Onset [° C.]] | Peak [° C.]] | Endset [° C.]] | Exothermy [J/g] |
| none (blank) | no | no | no | 0 |
| 1 | 116 | 138 | 150 | not measured |
| 3 | 100 | 131 | 135 | 279 |
| 10 | 100 | 126 | 132 | 129 |

The invention claimed is:

1. Compounds of the formula I:

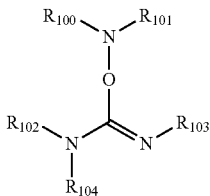

(I)

wherein $R_{100}$ and $R_{101}$ are each independently of one another a $C_1$-$C_4$ alkyl group or together form a radical of the formula A:

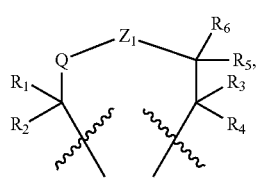

(A)

wherein
$R_1$-$R_4$ are each, independently of one another, a $C_1$-$C_4$ alkyl group;
$R_5$ and $R_6$ are each, independently of one another, hydrogen or a $C_1$-$C_4$ alkyl group;
Q is —($CR_7R_8$)—, wherein $R_7$ and $R_8$ are each, independently of one another, hydrogen or a $C_1$-$C_4$ alkyl group;
$Z_1$ is —($CR_{12}R_{13}$)—, where, independently of one another, one of the radicals $R_{12}$ and $R_{13}$ is hydrogen or a $C_1$-$C_4$ alkyl group and the other is —OH, a $C_1$-$C_6$ alkyl group, or a monoacyloxy group selected from the group consisting of a —O—C(=O)—H group, a —O—C(=O)—$C_1$-$C_4$ alkyl group, and a —O—C(=O)—$C_6$-$C_{10}$ aryl group;
$R_{102}$ and $R_{103}$ are each, independently of one another, a $C_1$-$C_4$ alkyl group, a cyclohexyl group, or an unsubstituted or $C_1$-$C_4$ alkyl group-substituted phenyl group; and
$R_{104}$ is hydrogen, a —C(=O)—$C_1$-$C_{17}$ alkyl group, or a —C(=O)—$C_6$-$C_{10}$ aryl group.

2. A process to prepare a compound of the formula I:

(I)

comprising the step of addition in a solvent of compound II and compound III:

(II)

(III)

wherein
$R_{100}$ and $R_{101}$ are each independently of one another a $C_1$-$C_4$ alkyl group or together form a radical of the formula A:

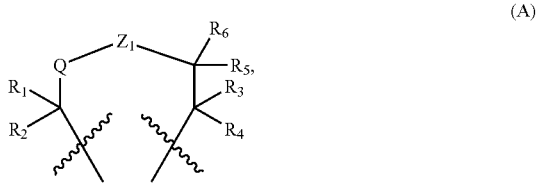

(A)

wherein
$R_1$-$R_4$ are each, independently of one another, a $C_1$-$C_4$ alkyl group;
$R_5$ and $R_6$ are each, independently of one another, hydrogen or a $C_1$-$C_4$ alkyl group;
Q is —($CR_7R_8$)—, wherein $R_7$ and $R_8$ are each, independently of one another, hydrogen or a $C_1$-$C_4$ alkyl group;
$Z_1$ is —($CR_{12}R_{13}$)—, where, independently of one another, one of the radicals $R_{12}$ and $R_{13}$ is hydrogen or a $C_1$-$C_4$ alkyl group and the other is —OH, a $C_1$-$C_6$ alkyl group, or a monoacyloxy group selected from the group consisting of a —O—C(=O)—H group, a —O—C(=O)—$C_1$-$C_4$ alkyl group, and a —O—C(=O)—$C_6$-$C_{10}$ aryl group; and
$R_{102}$ and $R_{103}$ are each, independently of one another, a $C_1$-$C_4$ alkyl group, a cyclohexyl group, or an unsubstituted or $C_1$-$C_4$ alkyl group-substituted phenyl group.

3. The process of claim 2, further comprising the step of alkylation or acylation by adding $R_{104}$-X, wherein $R_{104}$-X is either an alkylation agent comprising a $C_1$-$C_{19}$ alkyl group, a $C_5$-$C_{12}$ cycloalkyl group, a $C_7$-$C_{10}$ aralkyl halide, a sulfonate group, a trifluoromethanesulfonate group, a trialkyloxonium salt group; or $R_{104}$-X is an acylation agent comprising an acyl halide or an acyl anhydride.

4. A composition comprising:
  a) at least one ethylenically unsaturated polymerizable monomer or oligomer; and
  b) at least one compound of the formula I as defined in claim 1.

5. A process for preparing an oligomer, a cooligomer, a polymer, or a copolymer comprising subjecting the composition of claim 4 to free radical polymerization.

6. A process for lowering the molecular weight of polypropylene, a propylene copolymer, or a polypropylene blend comprising the steps of:
  a) adding at least one compound of the formula I as defined in claim 1 to a polypropylene, a propylene copolymer, or a polypropylene blend; and
  b) heating the mixture.

7. A method of using the compounds according to claim 1 comprising preparing a coating.

\* \* \* \* \*